United States Patent
Odell et al.

(10) Patent No.: US 9,255,918 B2
(45) Date of Patent: Feb. 9, 2016

(54) APPARATUS AND METHOD FOR OBTAINING GASEOUS HYDROGEN CONCENTRATIONS IN A MECHANICAL VACUUM PUMP GAS STREAM OF A BWR

(75) Inventors: Andrew D. Odell, Kennett Square, PA (US); Robert J. Scholz, Kennett Square, PA (US); James A. Tangen, Parsippany, NJ (US); Gerald F. Davina, Parsipanny, NJ (US); Joseph F. Giannelli, Parsipanny, NJ (US); Susan Elaine Garcia, Paso Robles, CA (US)

(73) Assignee: ELECTRIC POWER RESEARCH INSTITUTE, INC., Charlotte, NC (US)

( * ) Notice: Subject to any disclaimer, the term of this patent is extended or adjusted under 35 U.S.C. 154(b) by 733 days.

(21) Appl. No.: 13/478,953

(22) Filed: May 23, 2012

(65) Prior Publication Data

US 2013/0145819 A1    Jun. 13, 2013

Related U.S. Application Data

(60) Provisional application No. 61/489,497, filed on May 24, 2011.

(51) Int. Cl.
| | |
|---|---|
| *G01N 33/22* | (2006.01) |
| *G01N 1/24* | (2006.01) |
| *C01B 3/00* | (2006.01) |
| *G01N 33/00* | (2006.01) |

(52) U.S. Cl.
CPC .............. *G01N 33/0009* (2013.01); *C01B 3/00* (2013.01); *G01N 1/24* (2013.01)

(58) Field of Classification Search
CPC ......... C01B 3/00; G01N 1/24; G01N 33/0009
See application file for complete search history.

(56) References Cited

U.S. PATENT DOCUMENTS

| | | | |
|---|---|---|---|
| 3,788,813 A * | 1/1974 | Busch | 376/256 |
| 3,927,555 A * | 12/1975 | Godwin et al. | 73/31.01 |
| 3,977,232 A | 8/1976 | Hickam et al. | |
| 4,446,097 A | 5/1984 | Calabrese et al. | |
| 4,731,732 A * | 3/1988 | Warchol et al. | 702/24 |
| 4,918,974 A * | 4/1990 | Hachey et al. | 73/19.07 |
| 5,255,553 A * | 10/1993 | Hale et al. | 73/19.1 |
| 6,216,526 B1 * | 4/2001 | Junker et al. | 73/19.07 |
| 6,324,892 B1 * | 12/2001 | Nishina et al. | 73/23.2 |
| 2004/0099045 A1 * | 5/2004 | Demarest et al. | 73/23.2 |
| 2004/0112117 A1 * | 6/2004 | Wright et al. | 73/25.01 |
| 2004/0159149 A1 * | 8/2004 | Williams et al. | 73/152.23 |
| 2006/0233695 A1 | 10/2006 | Lawal et al. | |
| 2008/0292042 A1 | 11/2008 | Ishida et al. | |

OTHER PUBLICATIONS

Row, Thomas H. Radioactive waste systems and radioactive effluents. No. CONF-731120-1. Oak Ridge National Lab., Tenn.(USA), 1973.*

(Continued)

*Primary Examiner* — Lisa Caputo
*Assistant Examiner* — Punam Roy
(74) *Attorney, Agent, or Firm* — Trego, Hines & Ladenheim, PLLC

(57) ABSTRACT

An apparatus adapted to measure gaseous hydrogen concentrations in a mechanical vacuum pump (MVP) gas stream includes connection ports adapted to allow the apparatus to be connected to an MVP system and allow a gas stream sample to be taken from the MVP gas stream. The apparatus further includes a hydrogen concentration analyzer to measure $H_2$ concentrations of the gas stream sample taken from the MVP gas stream.

16 Claims, 21 Drawing Sheets

OTHER PUBLICATIONS

Stensvaag, John-Mark. "Regulating Radioactive Air Emissions from Nuclear Generating Plants: A Primer for Attorneys, Decisionmakers, and Intervenors."Nw. UL Rev. 78 (1983): 1.*

Takiguchi, Hideki, et al. "Evaluation of effectiveness of hydrogen water chemistry for different types of boiling water reactors." Journal of Nuclear Science and Technology 36.2 (1999): 179-188.*

GE BWR/4 Technology Manual, "Chapter 6.0 BWR Differences", 2002. Accessed online <http://pbadupws.nrc.gov/docs/ML0230/ML023010606.pdf>.*

Written Opinion of the International Searching Authority for PCT/US2012/039334. Jan. 2, 2013.*

* cited by examiner

APPARATUS AND METHOD FOR OBTAINING GASEOUS HYDROGEN CONCENTRATIONS IN A MECHANICAL VACUUM PUMP GAS STREAM OF A BWR

This application claims the benefit of Provisional Application No. 61/489,497 filed on May 24, 2011

BACKGROUND OF THE INVENTION

The oxidizing chemistry environment of BWR reactor water is a key factor in promoting intergranular stress corrosion cracking (IGSCC) of stainless steel and nickel based alloys used to construct reactor coolant system piping and vessel internals. Intergranular stress corrosion cracking in BWRs is typically mitigated during power operation with hydrogen water chemistry (HWC) or noble metal chemical addition with hydrogen water chemistry (NMCA+HWC).

However, these methods are only completely effective when the reactor is at power. Hydrogen injection is not placed into service until the reactor is at operating temperature and at a power greater than about 5% to 30%, depending on HWC system design. Consequently, the reactor water, which initially contains high dissolved oxygen levels from exposure to atmospheric air during cold shutdown, is oxidizing during heatup and low power operation. As a result, the highest crack growth rates currently occurs during start up, after refueling outages, before HWC becomes effective. Further, electrochemical corrosion potential (ECP) is very high.

Data indicates that IGSCC rates are higher at intermediate temperatures during plant startup and shutdown processes than at operating temperature. As a result, cracking can initiate and crack growth can occur during the plant shutdown process and startup from refueling or mid-cycle outages, when hydrogen injection is not in service. For units with NMCA+HWC, crack growth during the startup and shutdown processes may result in crack flanking, in which existing cracks can continue to grow even after hydrogen injection is on.

BRIEF SUMMARY OF THE INVENTION

These and other shortcomings of the prior art are addressed by the present invention, which provides an apparatus and method to measure % $H_2$ in an MVP gas stream to mitigate IGSCC.

According to one aspect of the invention, an apparatus adapted to measure gaseous hydrogen concentrations in a mechanical vacuum pump (MVP) gas stream includes connection ports adapted to allow the apparatus to be connected to an MVP system and allow a gas stream sample to be taken from the MVP gas stream. The apparatus further includes a hydrogen concentration analyzer to measure $H_2$ concentrations of the gas stream sample taken from the MVP gas stream.

According to another aspect of the invention, a method for determining gaseous hydrogen concentrations in a mechanical vacuum pump (MVP) system gas stream includes the steps of providing an apparatus adapted to measure gaseous hydrogen concentrations in the mechanical vacuum pump (MVP) system gas stream having a hydrogen concentration analyzer and first and second connection ports. The method further includes the steps of connecting the apparatus to the MVP system using the first and second connection ports, removing a gas stream sample from the MVP system gas stream, and using the hydrogen concentration analyzer to determine $H_2$ concentrations in the gas stream sample.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1A:
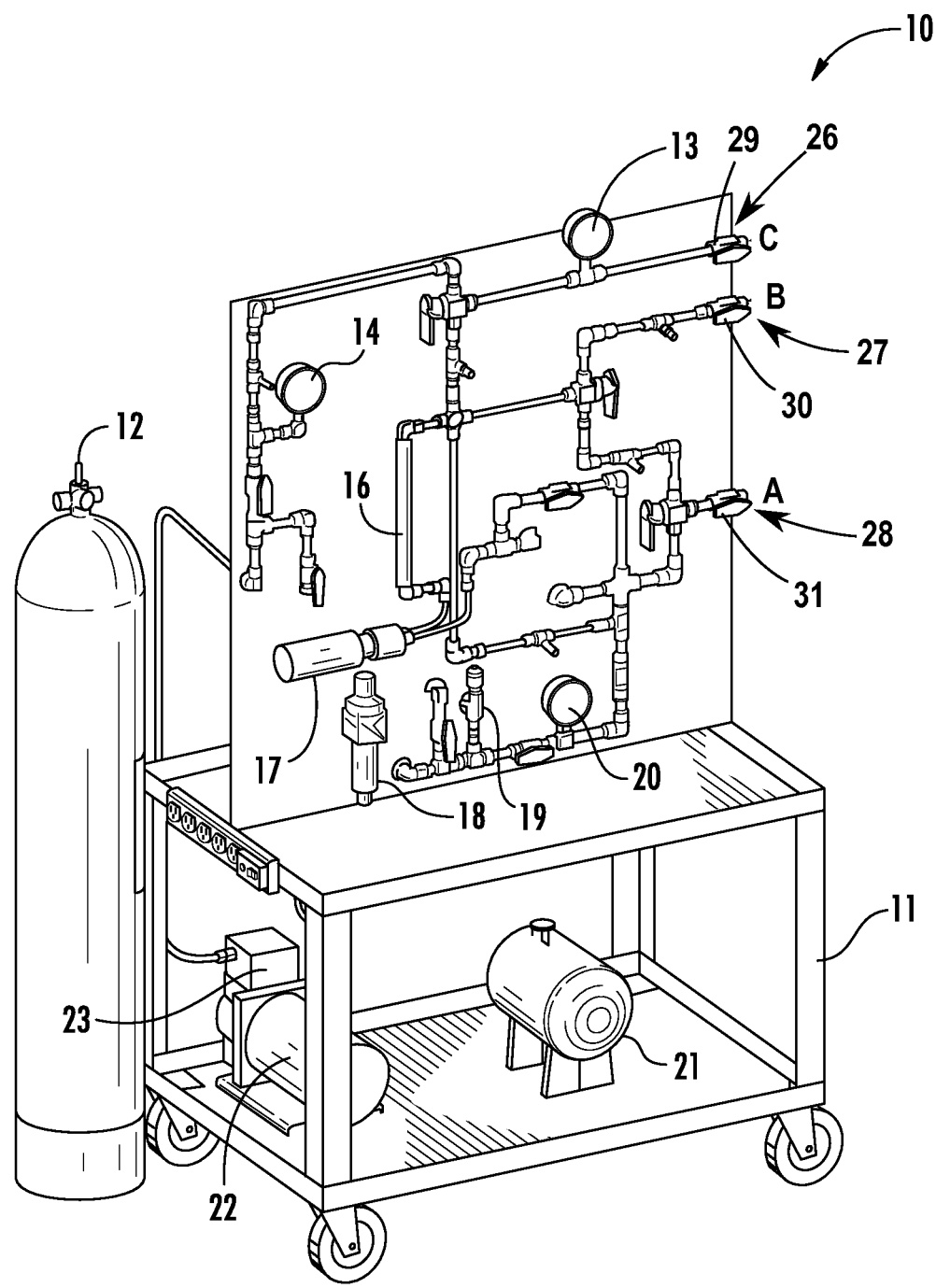
FIGS. 1A and 1B show an apparatus according to an embodiment of the invention.
Figure 1B:
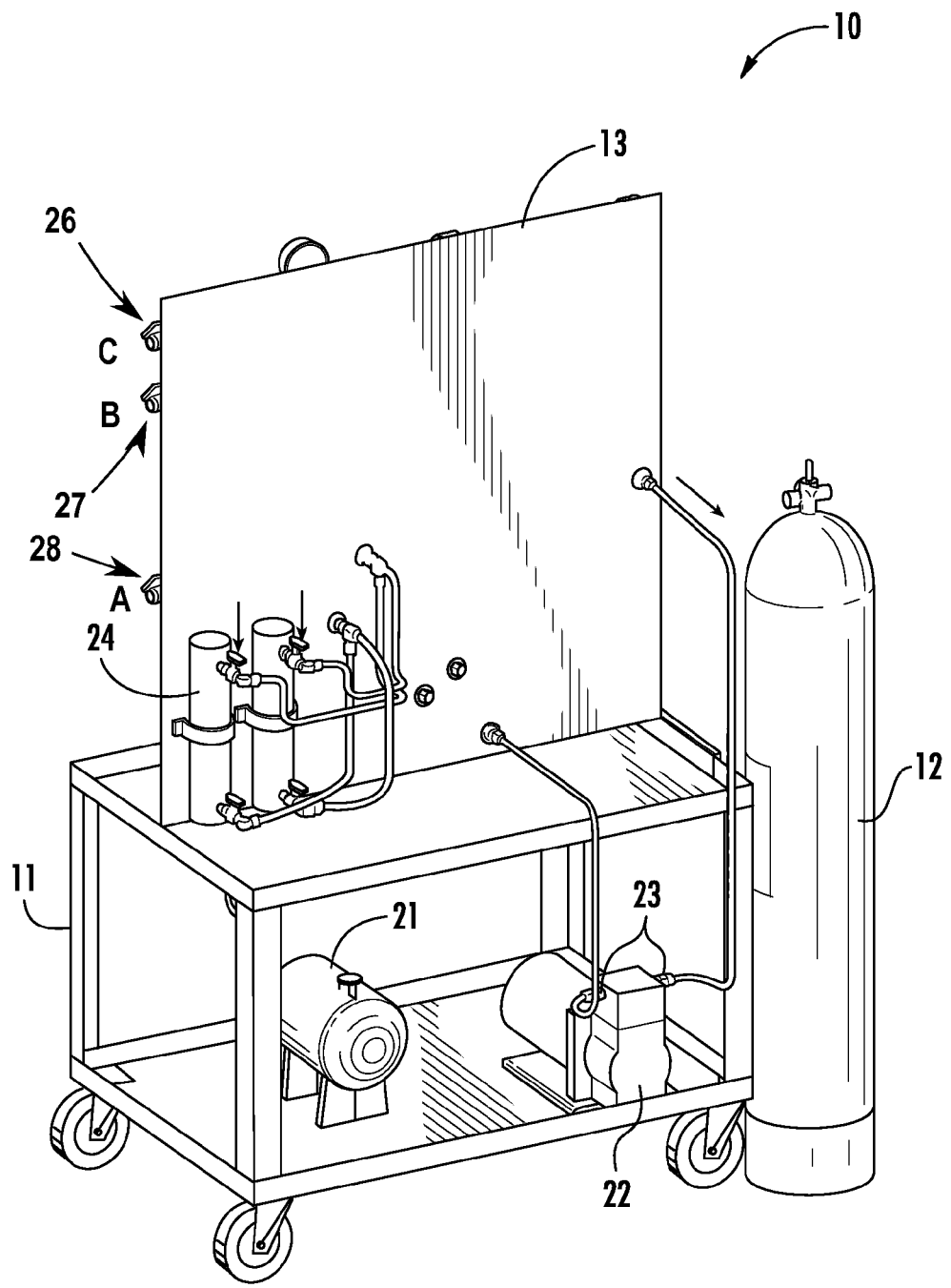

Referring to the drawings, an apparatus for measuring gaseous hydrogen concentrations in a mechanical vacuum pump (MVP) gas stream in accordance with an embodiment of the invention is illustrated in FIGS. 1A and 1B and shown generally at reference numeral 10. The apparatus 10 is an MVP sampling rig having a rolling cart 11 to allow the rig 10 to be easily transported to a desired site location, such as an MVP pump room, a nitrogen supply 12, an MVP suction pressure indicator 13 to monitor MVP suction pressure, a sample pump suction pressure indicator 14 to monitor pump suction pressure, an inline flow indicator 16, such as a rotometer, to monitor flow through the rig 10, an $H_2$ probe and flow chamber 17 (analyzer) to measure $H_2$ concentrations, an $N_2$ purge regulator 18 to regulate the pressure of $N_2$ going from the nitrogen supply 12 to the analyzer 17, a relief valve 19 to relieve pressure, a pump discharge pressure indicator 20 to monitor pump discharge pressure, a vacuum tank 21 for testing the rig 10, a vacuum pump 22 to draw samples from the MVP gas stream, inlet and outlet filters 23 to filter the sample MVP gas stream, desiccant columns 24 to dry wet gas samples, connection ports 26-28 having valves 29-31 to allow connection of the rig 10 to the MVP system and allow a sample to be taken from the MVP gas stream. The valves 29-31 allow the ports 26-28 to be selectively opened or closed to allow for a preferred sample flow path. A plurality of valves and tubing interconnecting all of the components listed above.

The MVP sample rig 10 may be used to identify condenser leaks during cold shutdown or early in plant startups. More particularly, the skid is used only when the MVP system is in service (prior to reactor startup to about 15% power). A gas (e.g., He or SF6) injected into a condenser water box and that leaks into the condenser may be measured in the MVP gas stream using an MVP sampling method, described below, with the appropriate sensor and analyzer to measure the injected tracer gas.

Generally, MVP systems have no flow measurement. The MVP sample rig 10 may be used to quantify the MVP flow by injecting a tracer gas into the condenser or MVP gas stream at a known rate using the measured concentration of injected gas to quantify the flow. During a plant startup, the MVP flow determined in this manner would provide a measure of air in-leakage prior to power ascension to the point where the normal offgas treatment system is in service. This would provide an early indication of high air in-leakage, which could prevent placement of the normal offgas system in service.

In general, the sampling method is used to obtain gaseous hydrogen concentration measurements in a Mechanical Vacuum Pump (MVP) gas stream. The rig 10 was designed, built and implemented for this purpose. The invention allows taking a sample from either the suction or discharge side of the MVP. The suction side (at vacuum) sample can be returned to the MVP suction or discharge or to atmosphere. The discharge sample can be returned to the MVP suction side or to atmosphere. The gas sample stream flows past a sensor to measure the concentration of a specific component in the gas stream. In the embodiment implemented, % $H_2$ in the gas was measured. Various sample configurations are shown in FIGS. 2-10—flow paths are denoted by heavier lines; numbering for FIG. 2 applies to FIGS. 3-10.

The sampling methodology is used to lower the ECP of boiling water reactor (BWR) vessel internals to mitigate intergranular stress corrosion cracking (IGSCC) during plant startups through chemical injection. The embodiment tested was under the conditions of no chemical injection to obtain baseline data on % $H_2$ concentration in preparation for a demonstration of a startup with hydrogen injection. The MVP has no sample points or % $H_2$ monitoring capability, but plant requirements state that the % $H_2$ should be below the flammability limit of $H_2$ gas in air.

The sample results provide the needed information to monitor the % $H_2$ in the gas when a chemical is injected during a BWR startup for ECP reduction of reactor piping and internal components to mitigate IGSCC. Chemicals injected into the reactor may include $H_2$, hydrazine, Carbohydrazide, alcohols or others.

Figure 2:
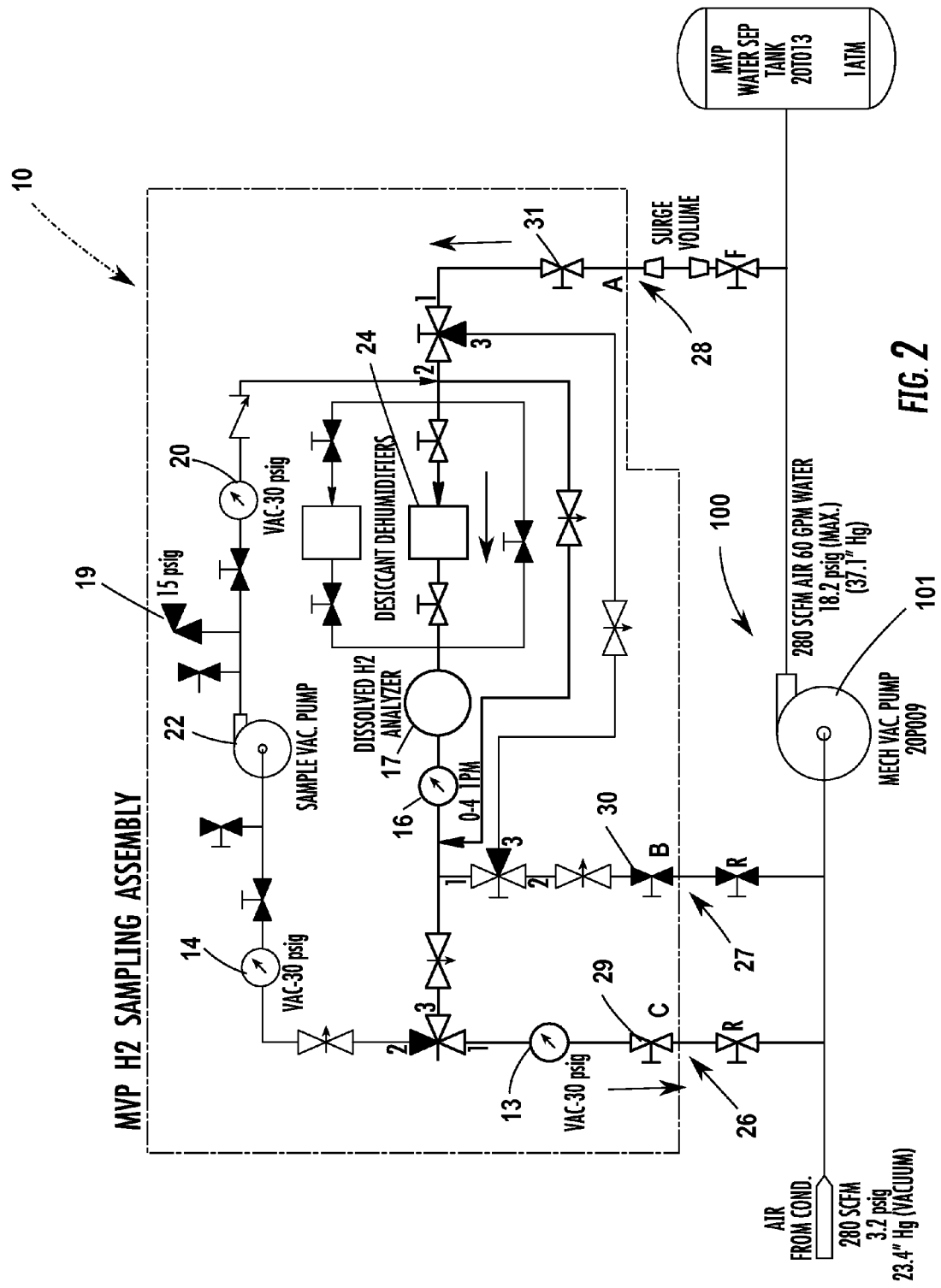
FIGS. 2-10 are piping and instrument drawings showing the apparatus of FIG. 1 connected to an MVP gas stream at various suction and discharge ports to measure % $H_2$.
Figure 3:
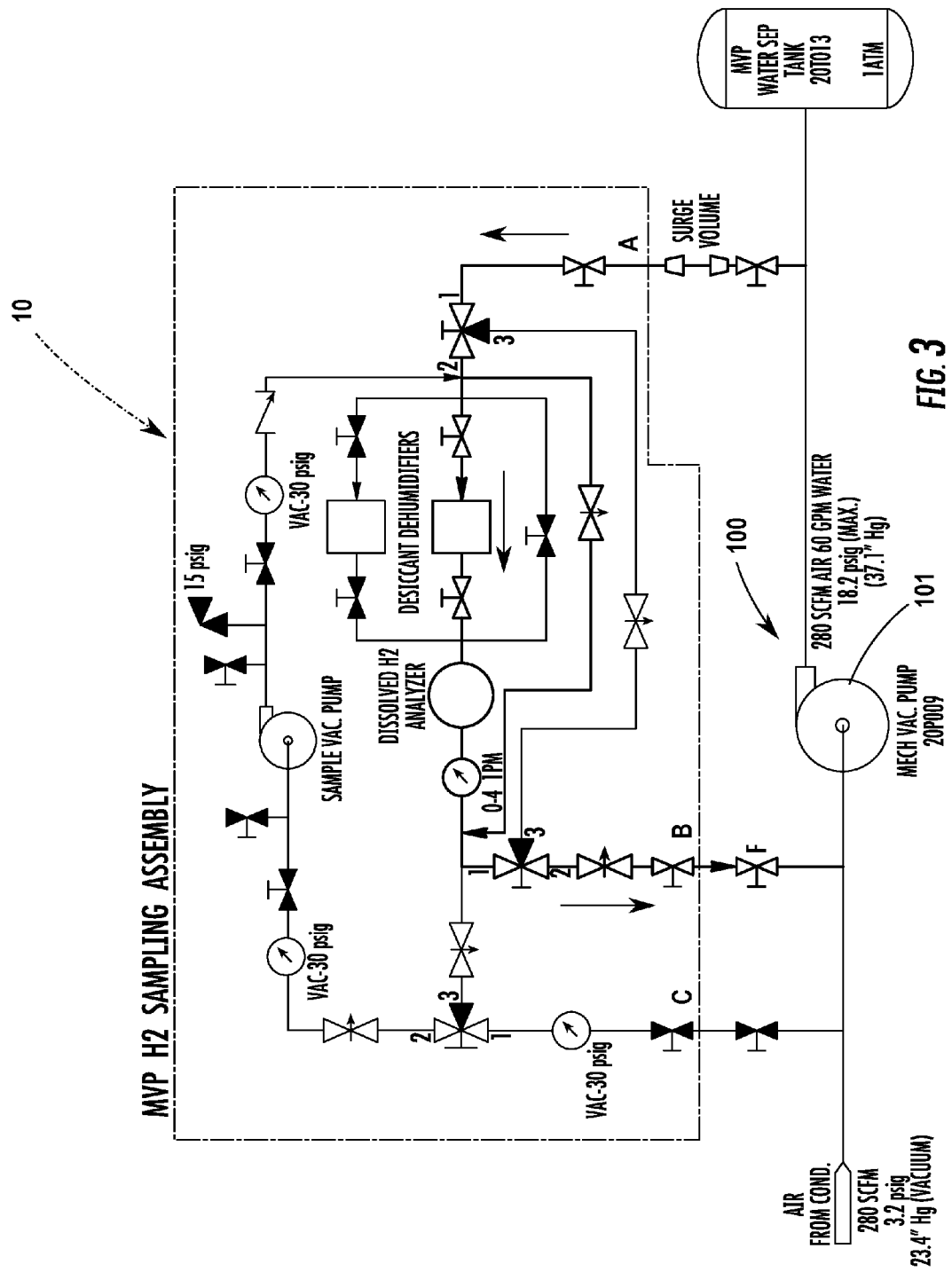
Figure 4:
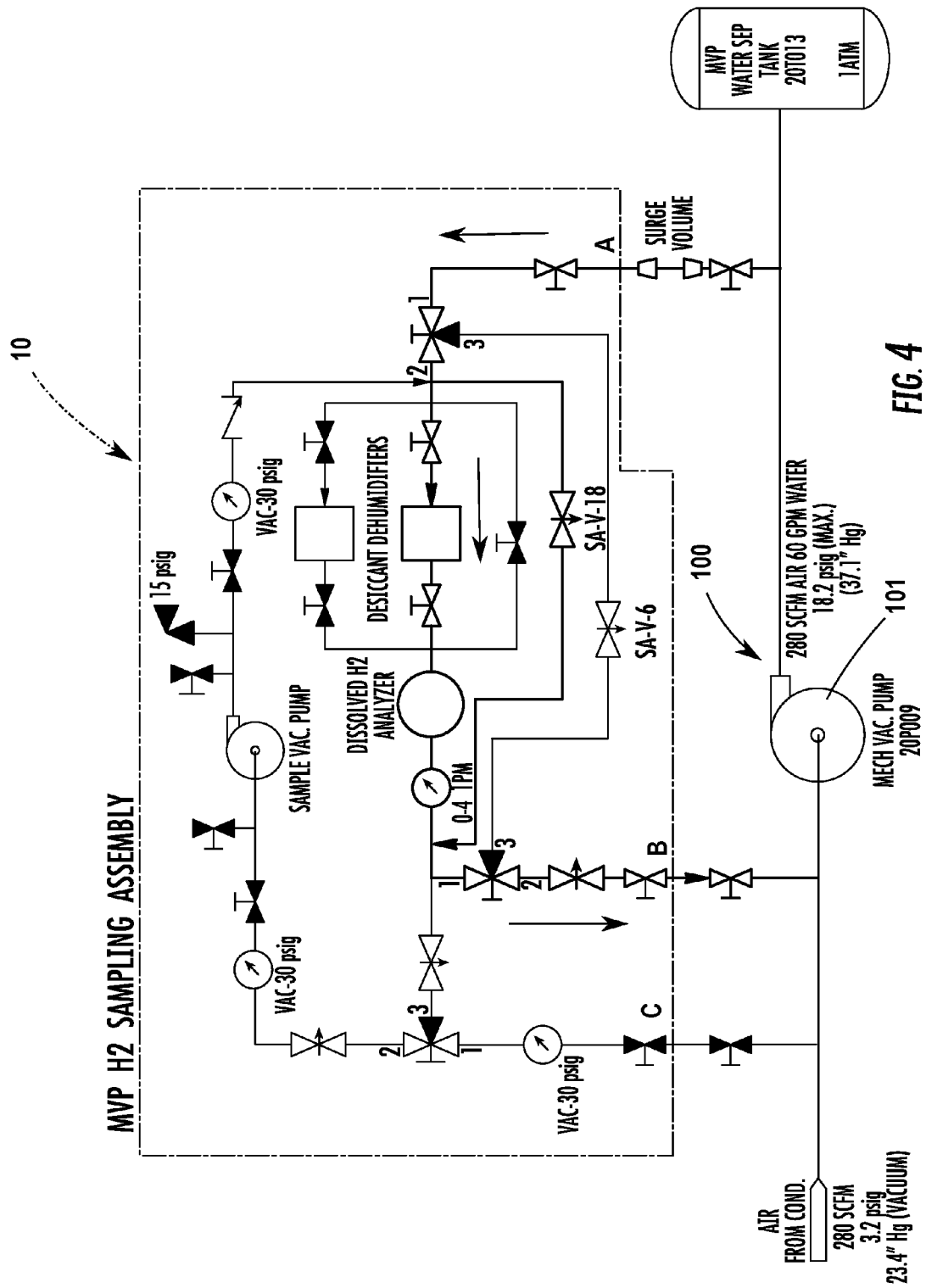
Figure 5:
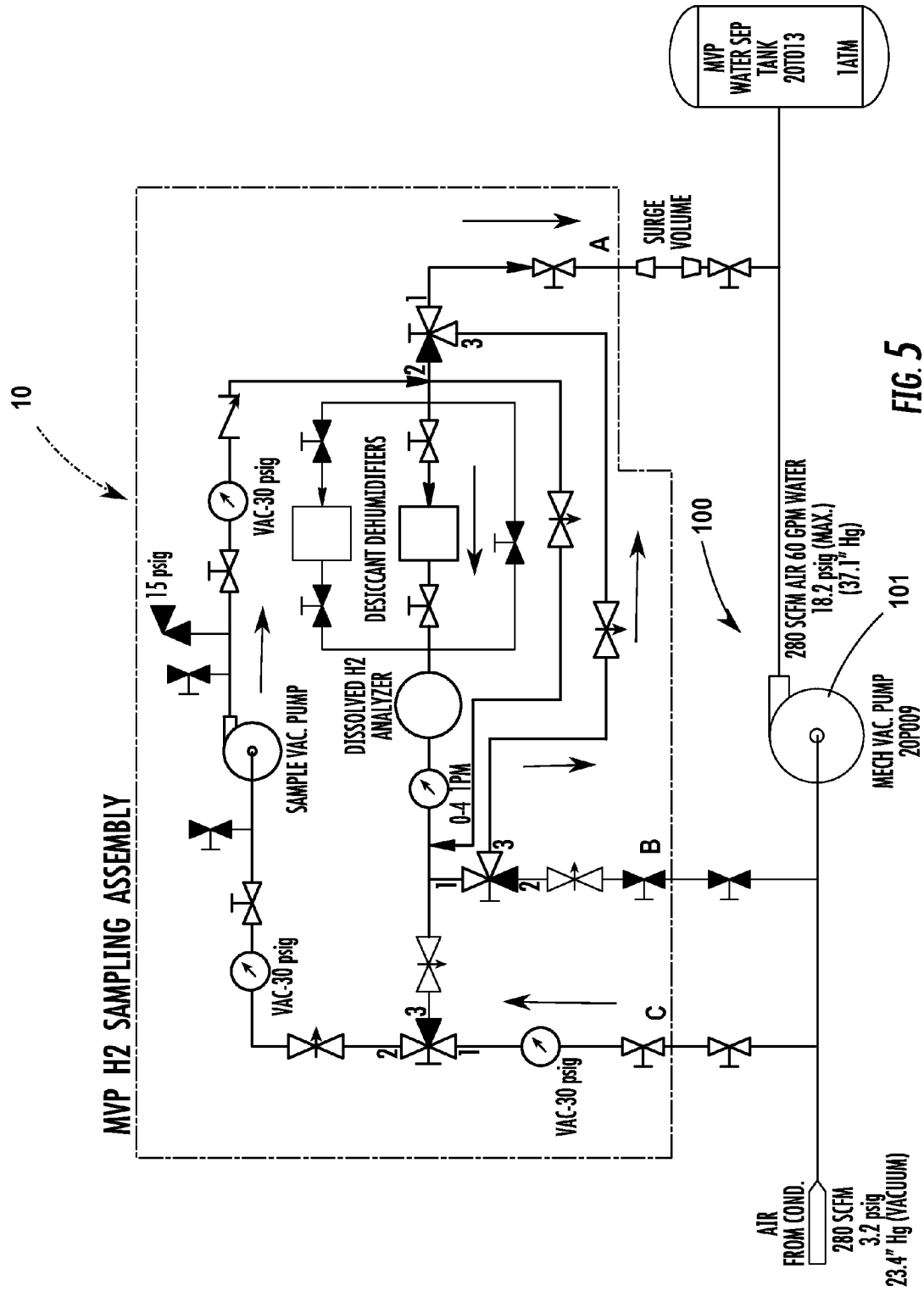
Figure 6:
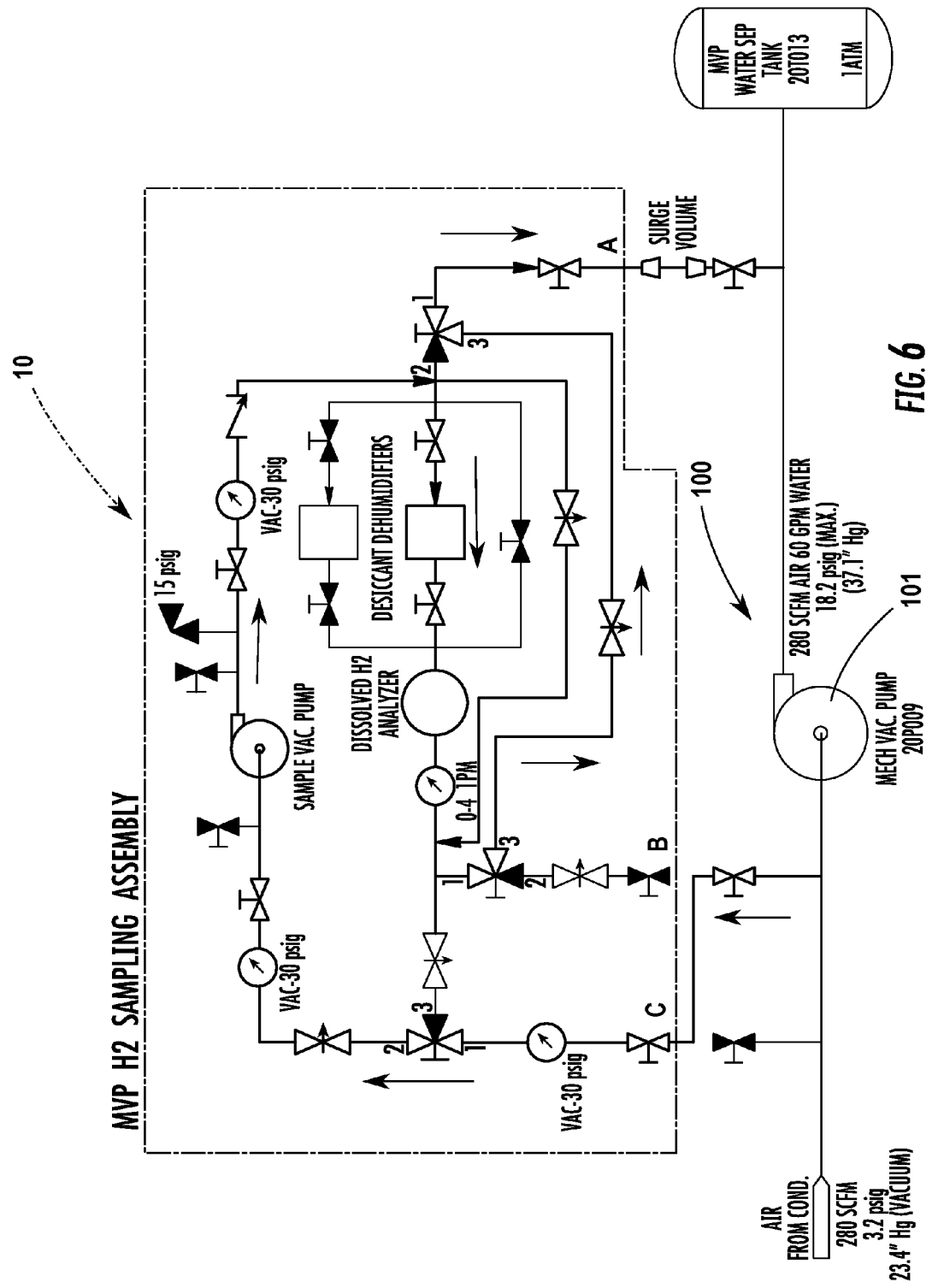
Figure 7:
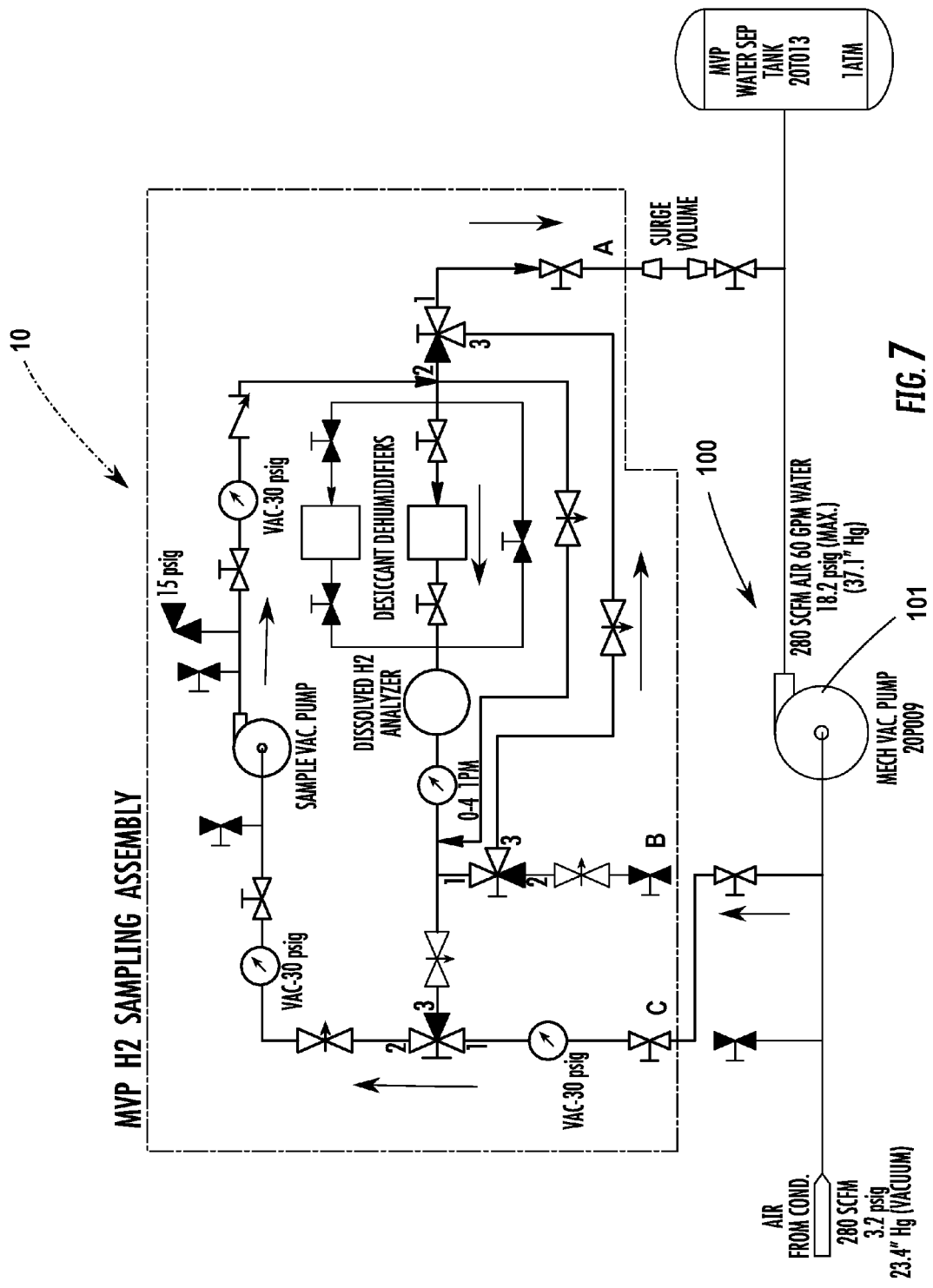
Figure 8:
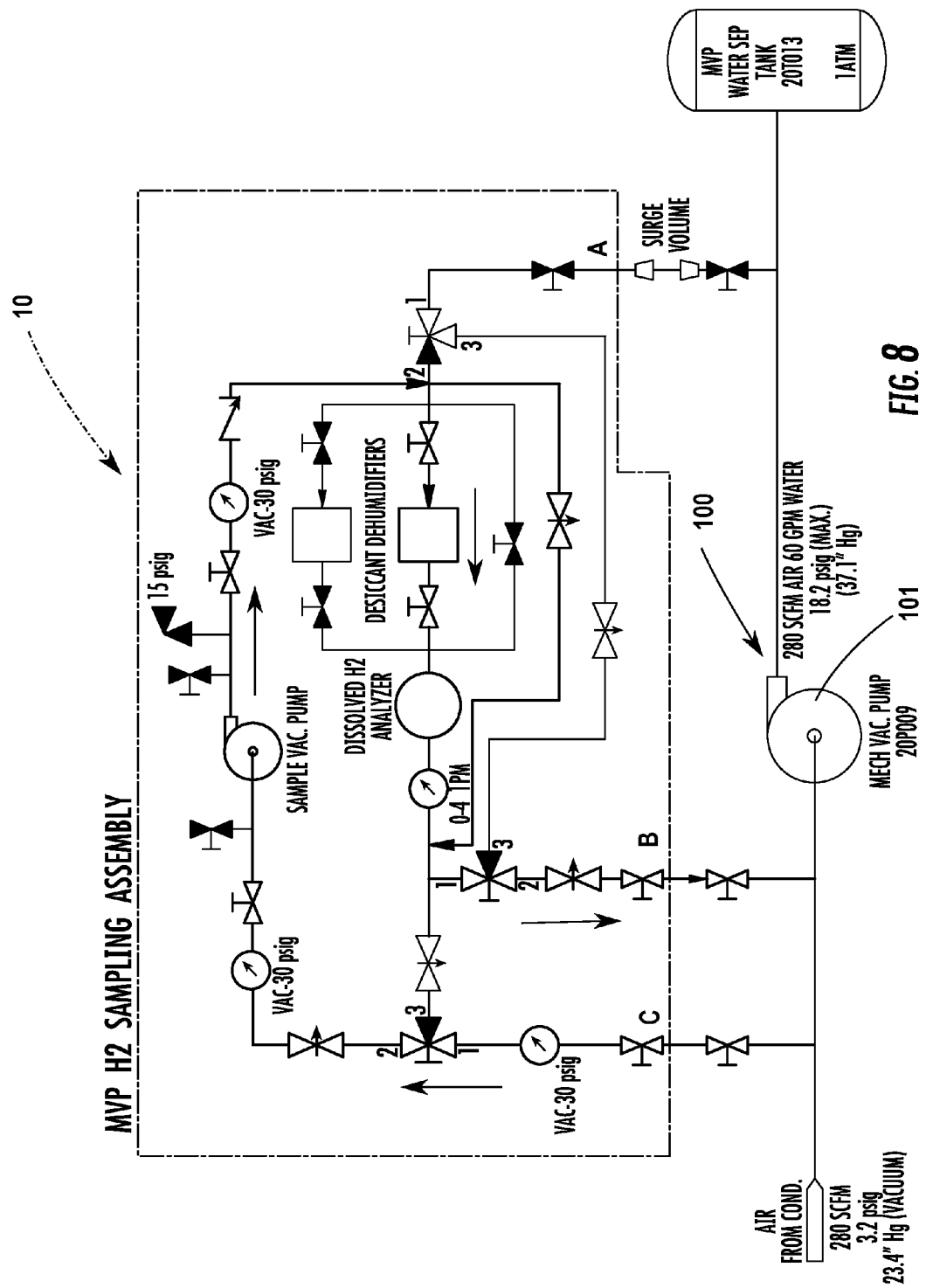
Figure 9:
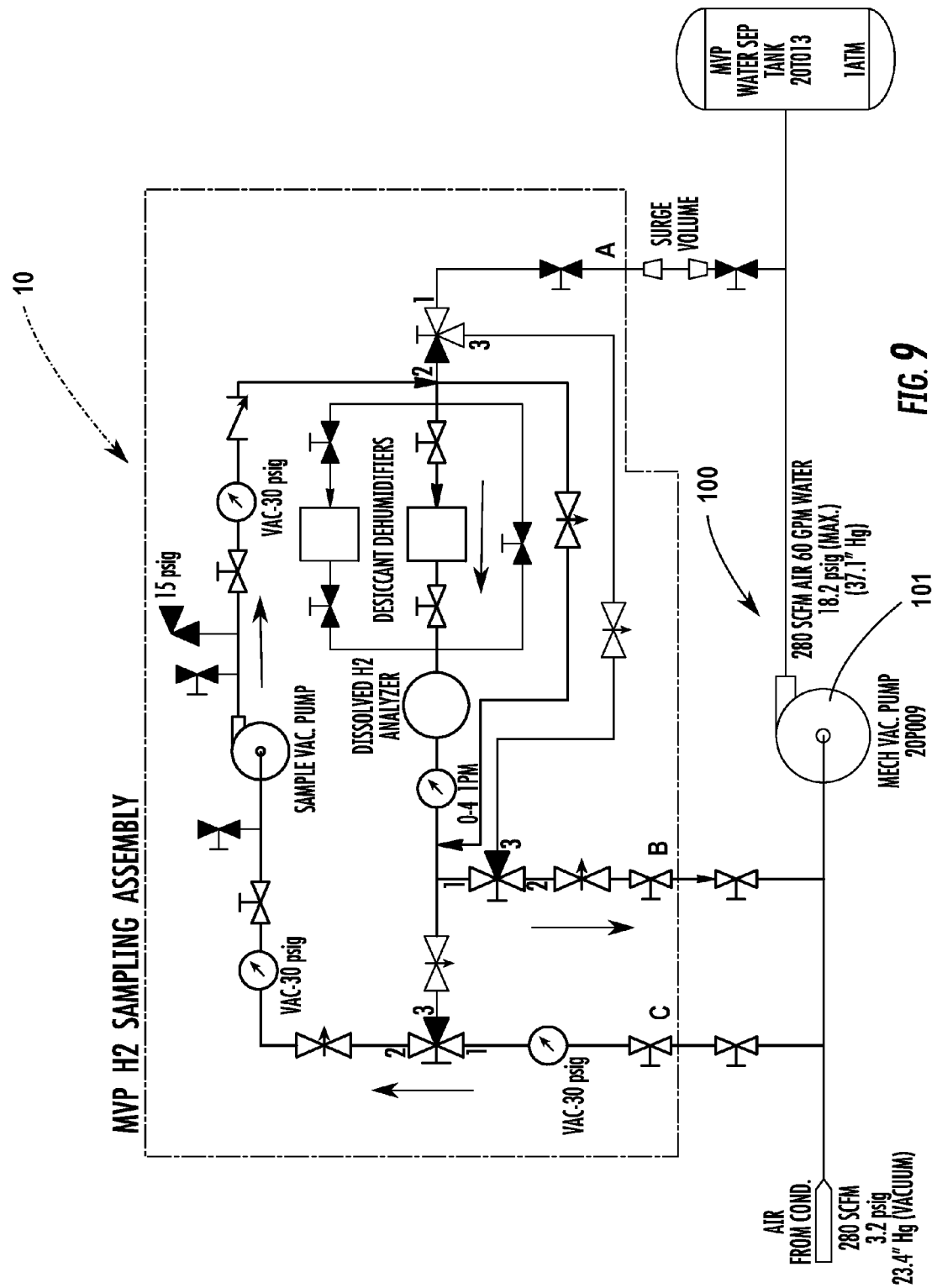
Figure 10:
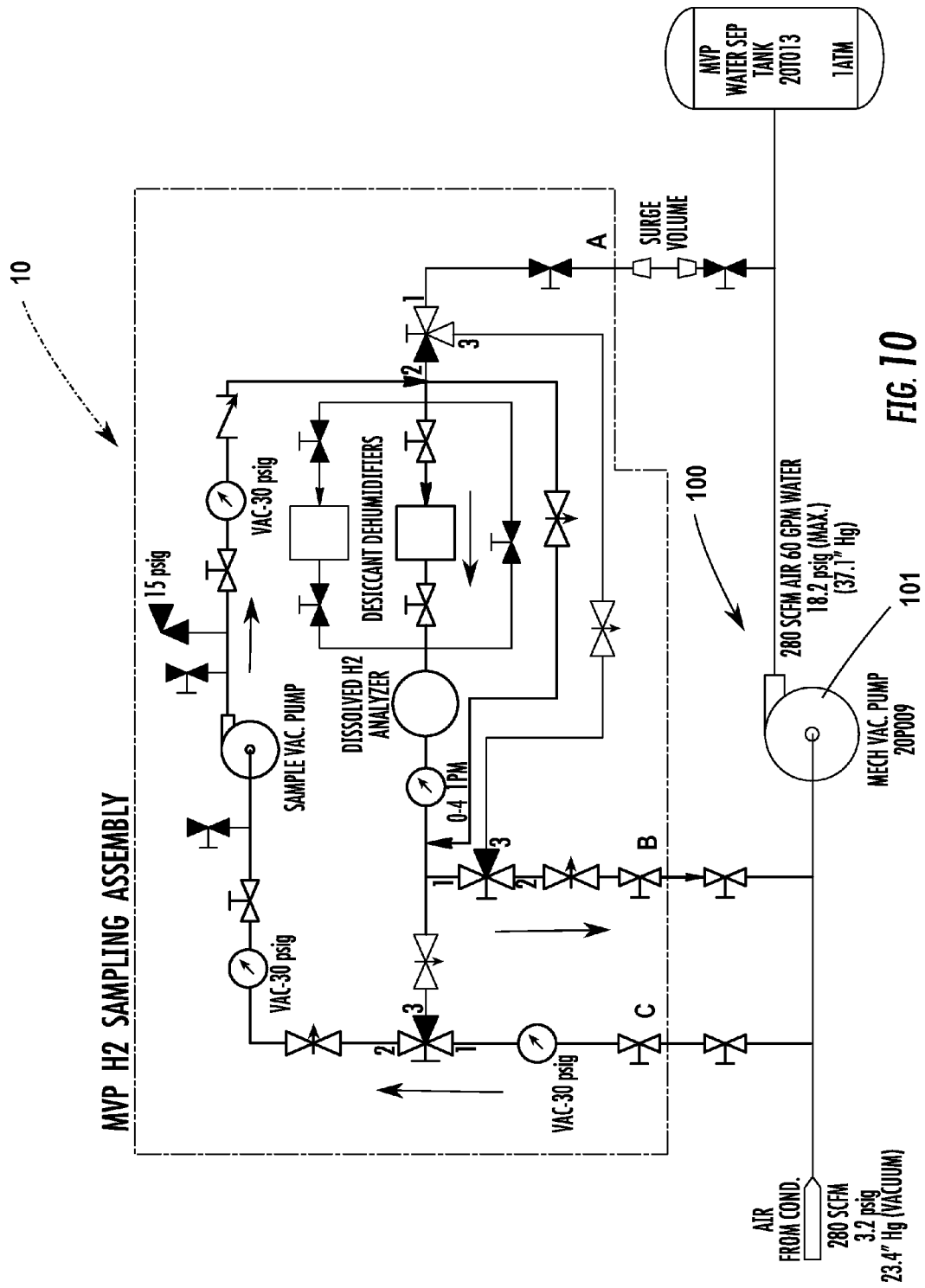
Figure 11:
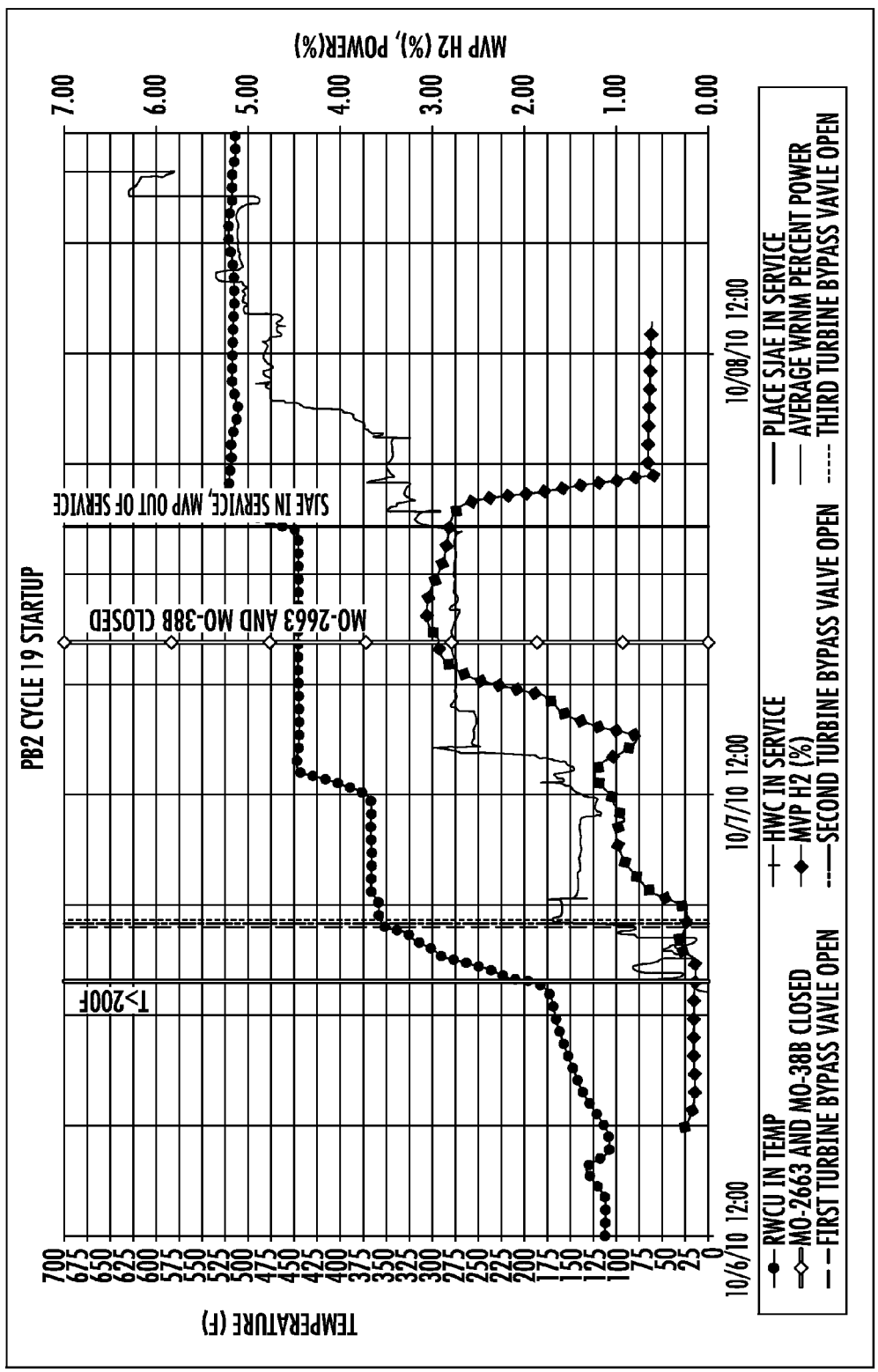
FIG. 11 is a graph showing MVP gas stream % $H_2$ concentrations.

More particularly, the sampling method is accomplished by connecting the rig 10 to an MVP system 100 having a mechanical vacuum pump 101. The rig 10 is connected to the MVP system 100 at corresponding points A, B, and C as shown on FIGS. 1A-10. In the most basic sampling methodology, the rig 10 pulls a sample from the MVP system 100 at point A (discharge side of pump 101) and returns the sample at point C (FIG. 2). The sample could also be returned at point B (FIG. 3). As shown, the sample flows through desiccant columns 24 to remove moisture from the sample and then proceeds to the $H_2$ probe or analyzer 17 to determine $H_2$ concentrations in the sample. The sample exits the probe 17 and flows through flow meter 16 which monitors the flow of the sample through the rig 10. If needed, the desiccant columns 24, analyzer 17 and flow meter 16 could be bypassed. The sample is then returned to the MVP system 100 at point C (suction side of pump 101). Prior to and after a sample has been taken, nitrogen from the nitrogen supply 12 is used to purge both the rig 10 and the $H_2$ probe 17 to reset $H_2$ probe at a zero measurement, thereby increasing its accuracy. In this sampling method, the pump 101 provides the necessary pressure to induce flow into the rig 10.

In the event that a sample is taken from the suction side of pump 101 (FIG. 8), vacuum pump 22 is employed to provide enough suction to remove the sample from the MVP system 100. As shown, in this scenario, the rig 10 pulls a sample from the MVP system 100 at point C (suction side of pump 101). The sample is pulled through indicators 13 and 14 by a suction side of vacuum pump 22 and is then discharged by the pump 22 such that the sample flows past relief valve 19 and indicator 20. The relief valve 19 opens if the pressure in the discharge line is too high to bring the pressure down to an acceptable level prior to reaching indicator 20. The sample then flows through the desiccant columns 24 to remove moisture, through the $H_2$ probe 17 to measure $H_2$ concentrations, through flow indicator 16, and is returned to the MVP system 100 at point B (suction side of pump 101). Again a nitrogen purge is used prior to and after sampling.

Description of MVP System

The mechanical vacuum pump (MVP) system is used during startup to establish condenser vacuum and will remain in service until off-gas and the steam jet air ejectors (SJAEs) are placed in service between 450 psig reactor pressure and 5% power. There is no MVP flow measurement. The off-gas system operating procedure provides a note to the operator that as off-gas flow is established; expect off-gas flow to exceed 200 scfm. This is because the initial flow to the SJAEs will be high as the inventory of gas in the condenser is reduced from the MPV steady-state pressure of ~3.4 psia to the SJAE steady-state pressure of ~1 psia.

Figure 12:
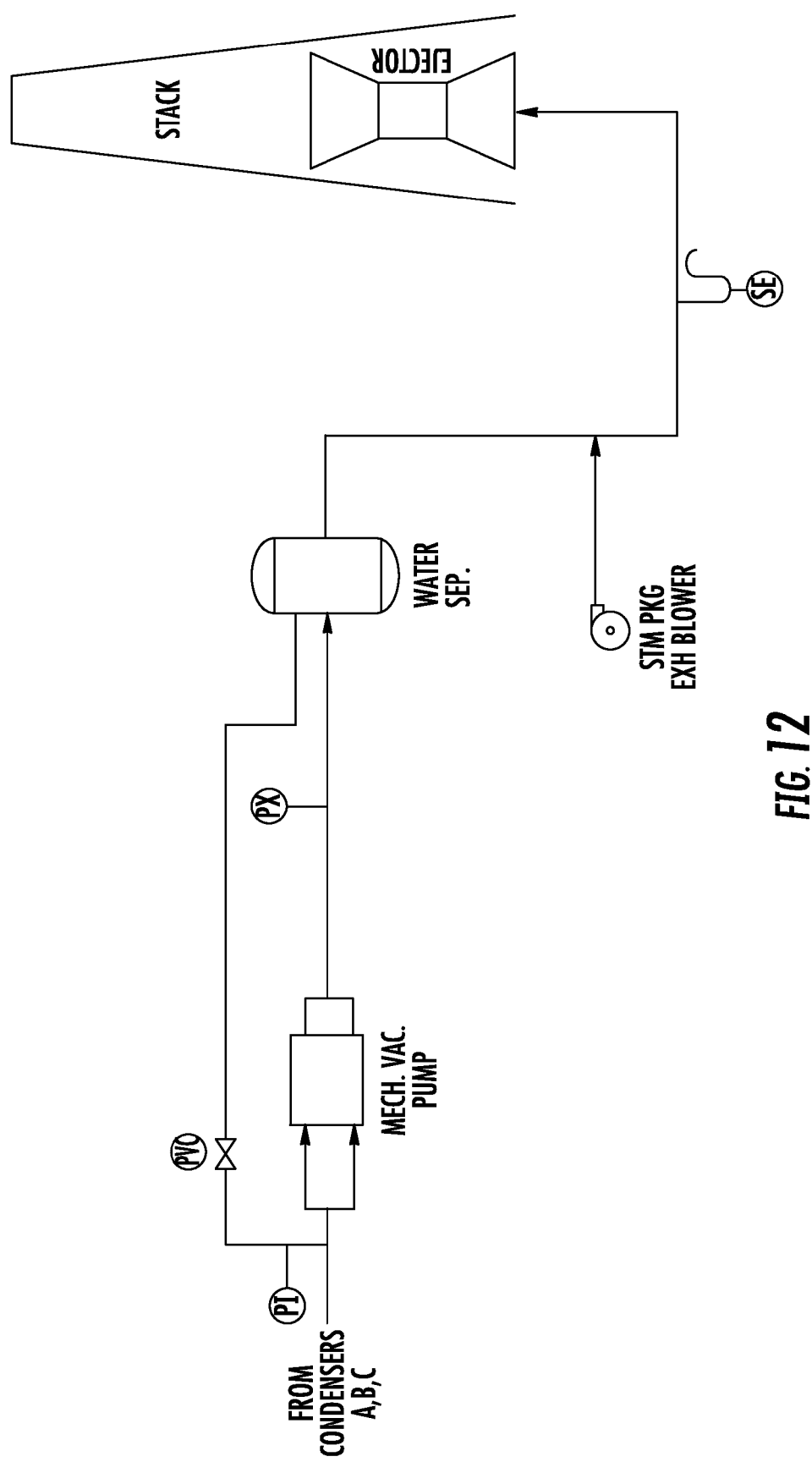
FIG. 12 is a flow diagram of an MVP in a BWR system.

The MVP was designed to remove the large volume of mostly air from the Main Condenser, which contains minimal amounts of hydrogen, activation gases and fission product gases, plus air in-leakage. The small amount of dissociated hydrogen and oxygen and low radioactivity in this mixture is the reason the off-gas need not be processed by the Off-gas Main Adsorber Bed. The MVP is not utilized during normal power operation due to the possibility of hydrogen combustion or detonation or exceeding the maximum permissible radioactivity release rates. A simplified flow diagram of the MVP is shown in FIG. 12.

The MVP is a rotary water ring pump that utilizes seal water as a liquid compressant to draw a vacuum. The MVP takes suction from the three Main Condensers through six lines, each containing a Condenser Side to Off-gas System valve. These lines combine into three off-gas suction lines, each containing a Condenser Off-gas to MVP valve. These three lines further combine into one line, containing a Condenser Off-gas Block Valve to MVP, prior to entry into the pump. The MVP then discharges the non-condensible gas and seal water mixture to the Mechanical Vacuum Pump Water Separator Tank, which removes entrained condensate from the non-condensible gases. The MVP discharge piping to the Main Stack provides a four minute holdup of the radioactive gases prior to discharge to the environment. The only valve in the discharge piping is a check valve at the exit of the Mechanical Vacuum Pump Water Separator Tank. The MVP discharge is routed to the Main Stack through a common holdup line with the operating Steam Packing Exhauster Blower discharge.

Valves and the MVP appear to be the only potential ignition sources in the MVP system as the only other equipment are a pressure indicator, a level gauge on the MVP Water Separator Tank and several pressure test points.

In the event of a low non-condensable gas flow rate to MVP condition, the Mechanical Vacuum Pump Recycle Pressure Control Valve opens to recirculate gas from the Mechanical Vacuum Pump Water Separator Tank back to the MVP suction to prevent pump or piping damage due to the possibility of isolated line operation. If required, the Condenser Vacuum Breaker Valves can be opened to dilute the off-gas flow by the introduction of air via the suction of the MVP.

Under normal startup conditions, without EHWC, the gas removed from the condenser by the MVP consists of hydrogen and oxygen from radiolysis, air in-leakage and water vapor. Hydrogen from EHWC would be additive to the hydrogen from radiolysis. The lower explosive limit for hydrogen in air is ~4% by volume. When this limit is exceeded, ignition or detonation can occur if the gas comes into contact with an ignition source. The ignition energy is very low (minimum ignition energy is 0.016 mJ@28% versus 0.21 mJ@8.5% for methane). All portions of the main condenser off-gas system are designed to withstand the effects of a hydrogen detonation without breach of the pressure boundary.

EXAMPLE

Atomic Power Station Off-Gas Recombiner System calculations were performed and provide off-gas flow rates with SJAE operation at the minimum load of 5% power. The design-basis air in-leakage rate is 54 scfm. This is equivalent to 60 cfm at 130° F. and 14.7 psia. The radiolysis rate was assumed directly proportional to power, to produce 12 cfm of radiolysis gas at 130° F./1 atm. This is equivalent to a rate of 0.064 scfm/MWt (60°/1 atm) at the rated power of 3293 MWt. By comparison, the design standard for off-gas systems in ANSI/ANS is 0.06 scfm/MWt. The water vapor flow rate was estimated by assuming a saturated gas mixture at the outlet of the secondary steam jet condenser (130° F. and 7.7 psia). The calculated values at 130° F. and 14.7 psia are 8 cfm hydrogen, 4 cfm oxygen, 60 cfm air and 27.9 cfm vapor. This results in a hydrogen concentration of approximately 8% in this mixture.

If the MVP were in service up to 5% reactor power, as allowed per design, the same flow rates of non-condensible gases as given above would exist. The volume fraction water vapor, assuming ideal gas behavior, would be $p_v/(P_t-p_v)$, where $p_v$ is the vapor pressure at condenser temperature, and $P_t$ is the condenser pressure. At 100° F. ($p_v$=0.949 psia) and 3.4 psia condenser pressure (conditions measured during the startup of Peach Bottom 3), the volume fraction vapor would be 0.39. This is equivalent to ~28 cfm vapor at 130° F. and 14.7 psia, which for these condenser conditions is essentially equal to that calculated above. The hydrogen concentration would be approximately 8%. Although the water vapor fraction will vary with changes in condenser conditions, this suggests that at 5% power the mass flow of water vapor will be about the same in the air removal section of the main condenser as in the SJAE after-condenser outlet.

For comparison to original design operations without hydrogen addition, the Process Diagram Off-Gas Recombiner System—indicates that at 100% power with 60 cfm air in-leakage at 130° F. and 14.7 psia, the off-gas at the outlet of the SJAE after-condenser contains 154 cfm hydrogen, 77 cfm oxygen and 52.1 cfm vapor. This diagram is for no hydrogen addition, and under Hydrogen Water Chemistry (HWC) conditions there would be less hydrogen. Under these conditions and at this location, the off-gas contains approximately 45% hydrogen. The hydrogen concentration would be lower in the air removal section of the main condenser due to higher water vapor flow. The concentration of hydrogen is reduced to near 4% after the off-gas system jet compressor by the addition of dilution steam.

The hydrogen and oxygen produced by radiolysis increases with increasing reactor power. ANSI/ANS gives a design gas generation rate for radiolysis of 0.06 scfm/MWt at 60° F. and 1 atm. The average radiolysis gas generation rate, based on measurements at a number of plants, is 0.041 scfm/MWt. The radiolytic gas generation rate is assumed to be proportional to power. Two thirds of the radiolytic gas by volume would be hydrogen and one third oxygen.

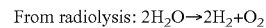

From radiolysis: $2H_2O \rightarrow 2H_2 + O_2$

Using the ANSI/ANS gas generation rate, the hydrogen and oxygen gas generation rates are:

$$\text{Rate } H_2 \text{ Generation} = \frac{2}{3} \times \frac{0.06 \text{ scfm}}{MW_t} \times MW_t$$

$$\text{Rate } O_2 \text{ Generation} = \frac{1}{3} \times \frac{0.06 \text{ scfm}}{MW_t} \times MW_t$$

A calculation method was set up to generate estimates of hydrogen concentrations in the off-gas to the MVP under startup conditions with EHWC.

Assumptions:
1. Steady state conditions at each power level evaluated.
2. Complete and instantaneous mixing of gases in the condenser.
3. Condenser Off-gas is assumed to be saturated with water vapor.
4. Water vapor is treated as an ideal gas.
5. Radiolysis of water is linear with reactor power.
6. No suppression of radiolysis of water due to hydrogen injection.
7. Design air in-leakage rate is 54 scfm.
8. Standard temperature and pressure are 70° F. and 14.7 psia, respectively.
9. No consumption of hydrogen through reactions with oxidants.
10. Condenser temperature and pressure are 100° F. (assumed) and 3.4 psia (approximate condenser pressure during Peach Bottom 3 Cycle 18 startup), respectively.

Figure 13:
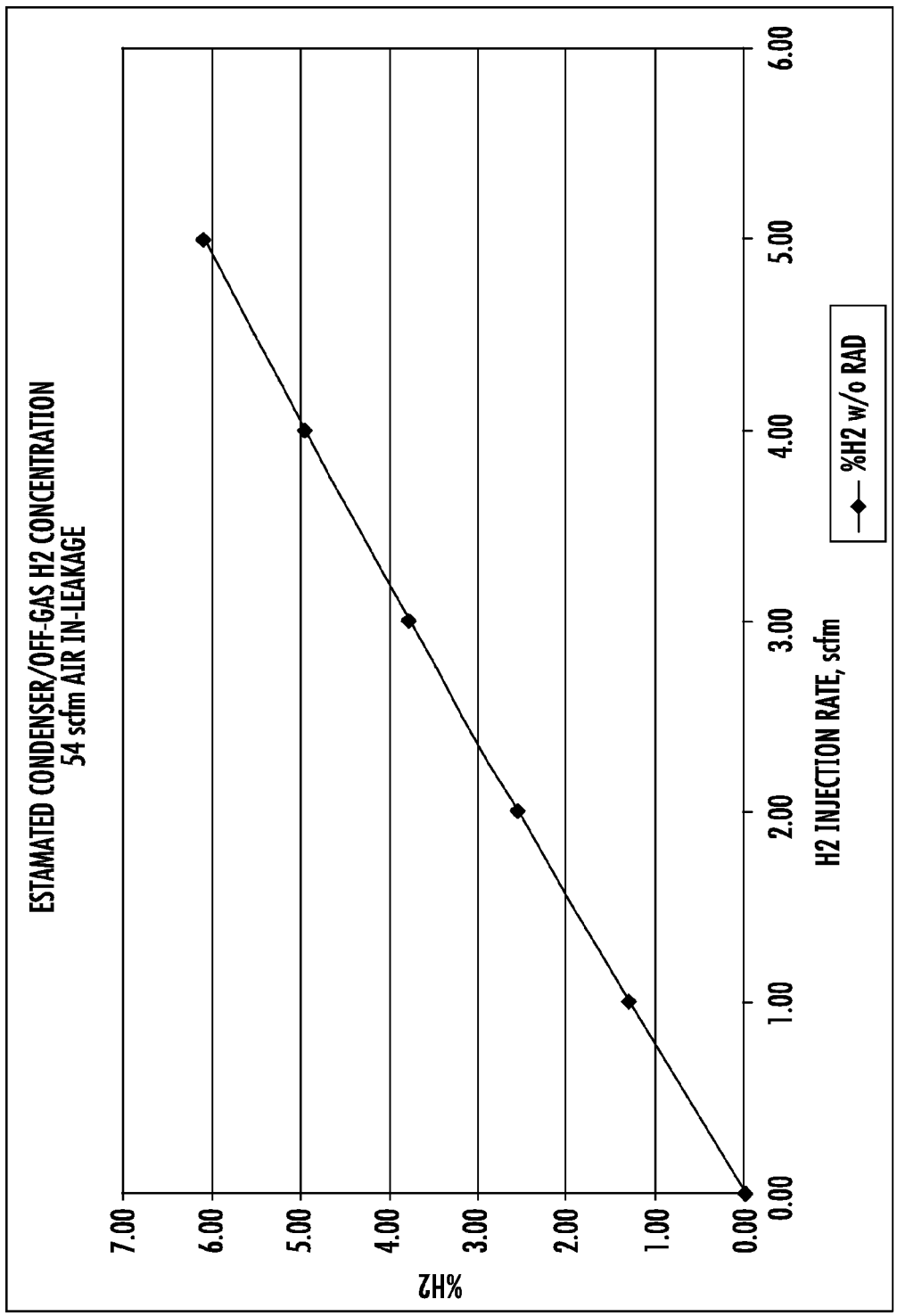
FIG. 13 shows estimated condenser/off-gas hydrogen concentration as a function of hydrogen injection rate at reactor shutdown.

The results of the calculations for hydrogen injection rates from 0 to 5 scfm prior to pulling rods are shown in FIG. 13. For this case, when the reactor is shutdown and there is no or little hydrogen generation from radiolysis, injecting 5 scfm hydrogen results in an estimated hydrogen concentration in the condenser air removal section of approximately 6.11%. This is below the estimated hydrogen concentration of 8.0%, based on the design air in-leakage rate and ANSI/ANS hydrogen generation rate of 7.2 scfm when the reactor is at 5% power without hydrogen injection. Therefore, injecting up to 5 scfm hydrogen when the reactor is shut down would result in a hydrogen concentration in the condenser/off-gas below that which is expected at 5% reactor power during startup at the design air in-leakage rate.

During hydrogen injection for EHWC, as reactor power increases and radiolysis increases, an initial limiting hydrogen concentration of less than or equal to 8.0% could be established based on the estimated hydrogen concentration from radiolysis when the reactor is at 5% power at the design air in-leakage rate. However, this would limit the hydrogen injection rate to 0 scfm at 5% power since 7.2 scfm hydrogen from radiolysis at 5% power yields 8% hydrogen in the off-gas. If a safety factor should be applied to ensure this concentration is not exceeded it would further limit the hydrogen injection rate. Additionally, since this is based on the design air in-leakage rate of 54 scfm, if the air in-leakage rate is near the expected normal in-leakage rate of approximately 24 scfm, the hydrogen injection rate would be limited further. Therefore, it may be necessary to establish a method to introduce air into the condenser or at the off-gas lines out of the condenser to maintain the hydrogen concentration below the limit established for EHWC.

Figure 14:
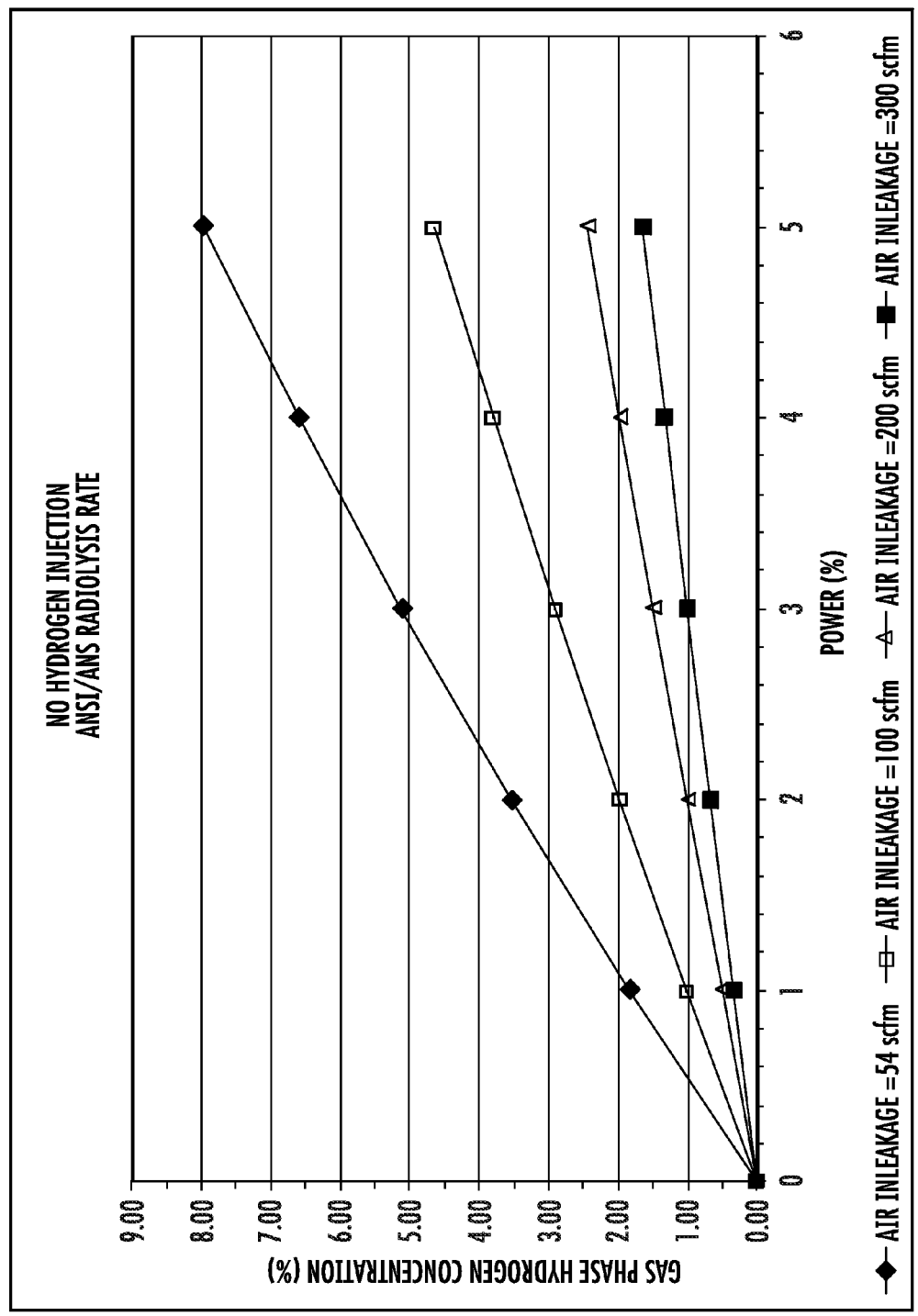
FIG. 14 shows estimated condenser/off-gas hydrogen concentration as a function of power with no hydrogen injection.
Figure 15:
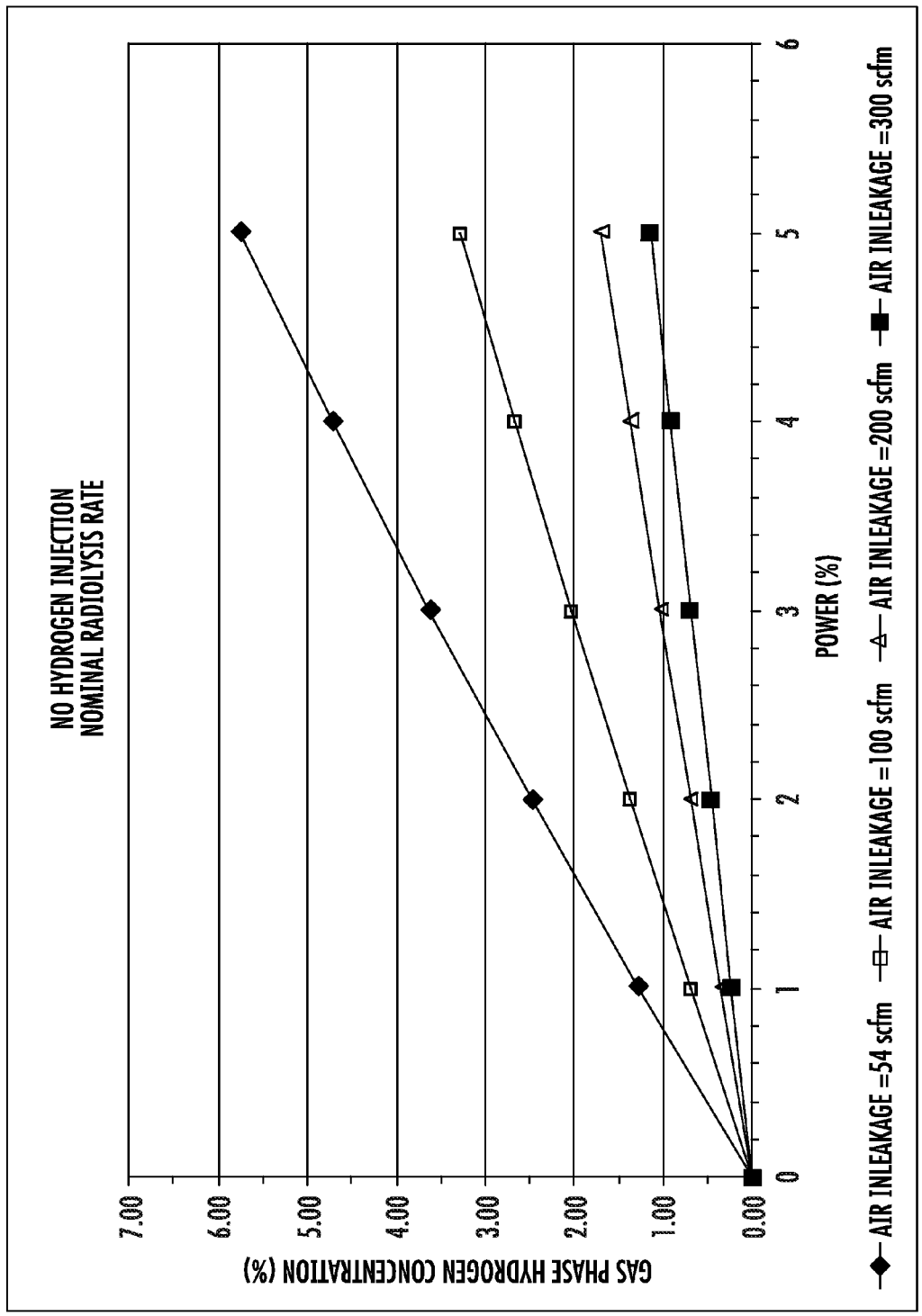
FIG. 15 shows estimated condenser/off-gas hydrogen concentration as a function of power with no hydrogen injection.

The actual hydrogen concentration in the condenser/off-gas during startup up to 5% power is highly dependent on the air in-leakage rate. The calculated hydrogen concentration as a function of power and air in-leakage, with no hydrogen injection, is shown in FIG. 14. The calculated maximum hydrogen concentration from radiolysis gas generation, based on the ANSI/ANS rate, at the design basis air in-leakage rate of 54 scfm is 8.0%. However, as noted previously, the nominal radiolysis rate is ~⅔ of the ANSI/ANS design rate. The calculated maximum hydrogen concentration from radiolysis gas generation, based on the nominal rate, at the design basis air in-leakage rate of 54 scfm is 5.75%, as shown in FIG. 15. The plant has indicated that air in-leakage is usually high (>100 scfm) during startup. Therefore, the actual hydrogen concentration may be below 4% up to a power level of 5% without hydrogen injection. Measurement of the hydrogen concentration at the MVP during a normal startup, without hydrogen injection, would provide operating data to quantify the hydrogen concentration and to estimate the air in-leakage rate.

Figure 16:
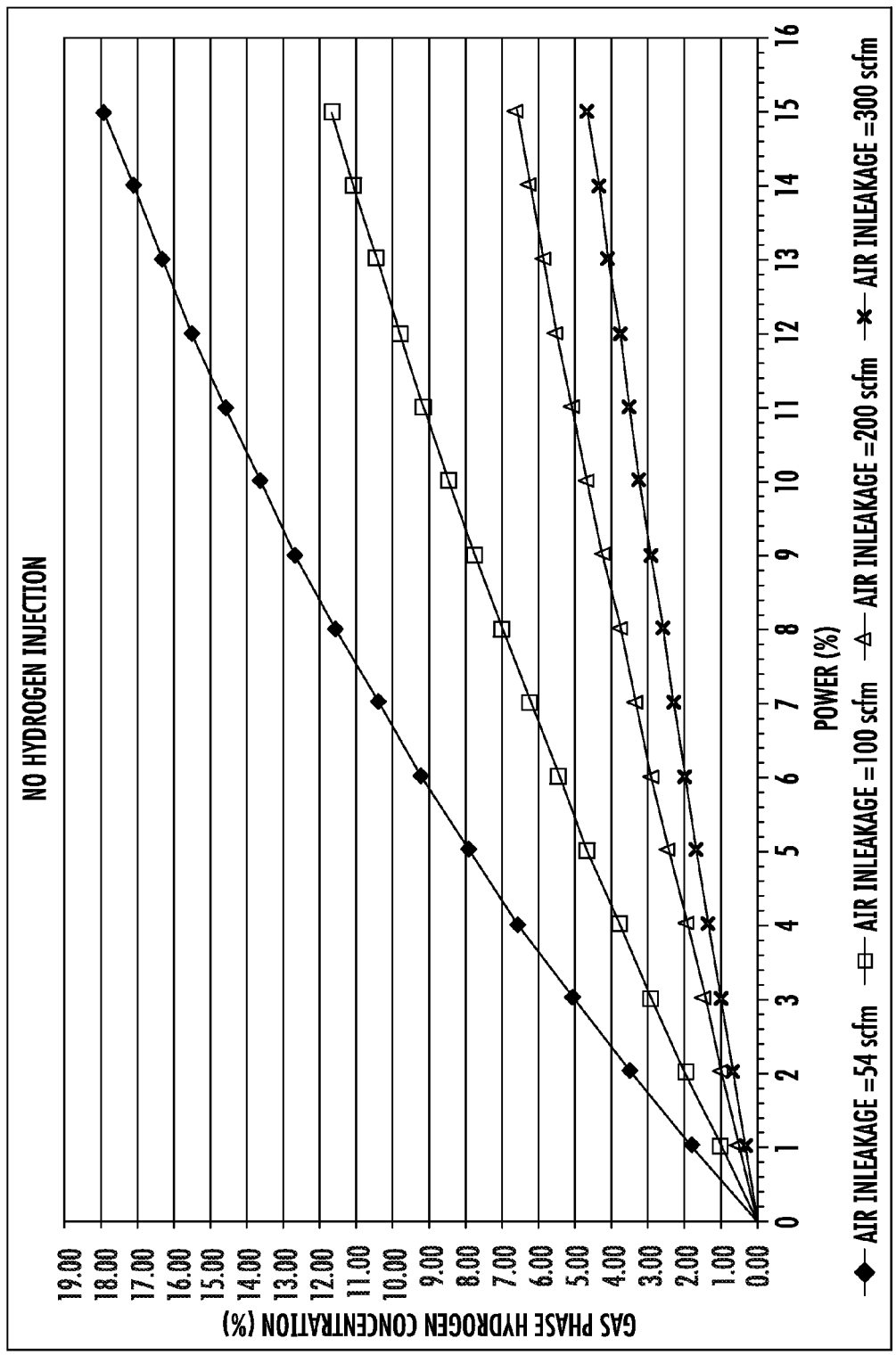
FIG. 16 shows estimated condenser/off-gas hydrogen concentration as a function of power with no hydrogen injection.

The normal HWC system is typically placed in service prior to reaching 15% power during a plant startup. The calculated hydrogen concentration in the condenser/off-gas as a function of power and air in-leakage, with no hydrogen injection, is extended to 15% power in FIG. 16. At the design air in-leakage rate of 54 scfm, the calculated hydrogen concentration is approximately 18% at 15% power. Even if hydrogen is added, this condition is bounded by conditions at 100% power under Normal Water Chemistry (NWC). At 100% power with NWC, the hydrogen concentration would be 45% (from the Process Diagram), and the expected hydrogen concentration would be 39% based on the nominal radiolysis rate.

Figure 17:
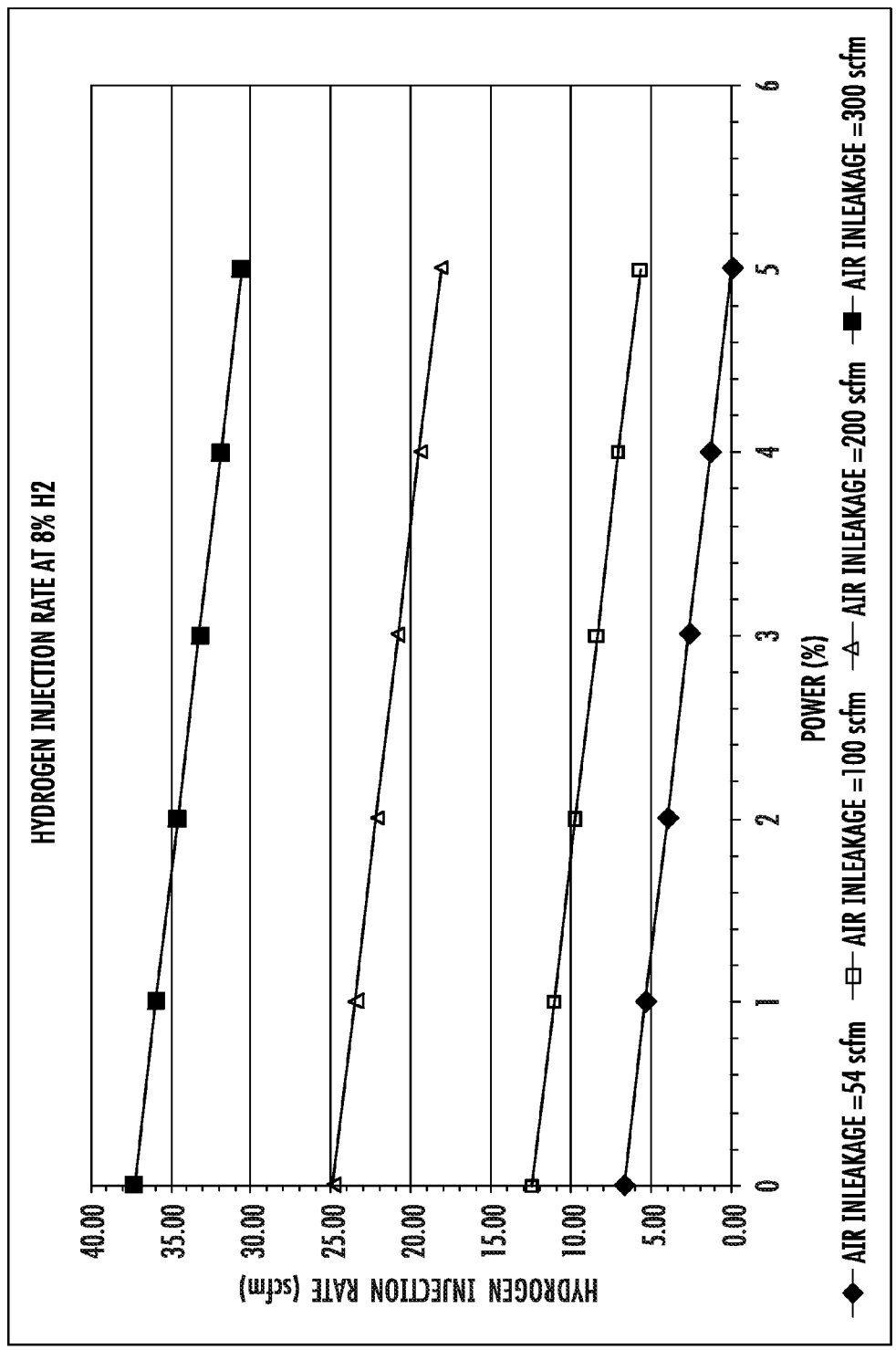
FIG. 17 shows estimated hydrogen injection rate for 8% $H_2$ condenser/off-gas hydrogen concentration.
Figure 18:
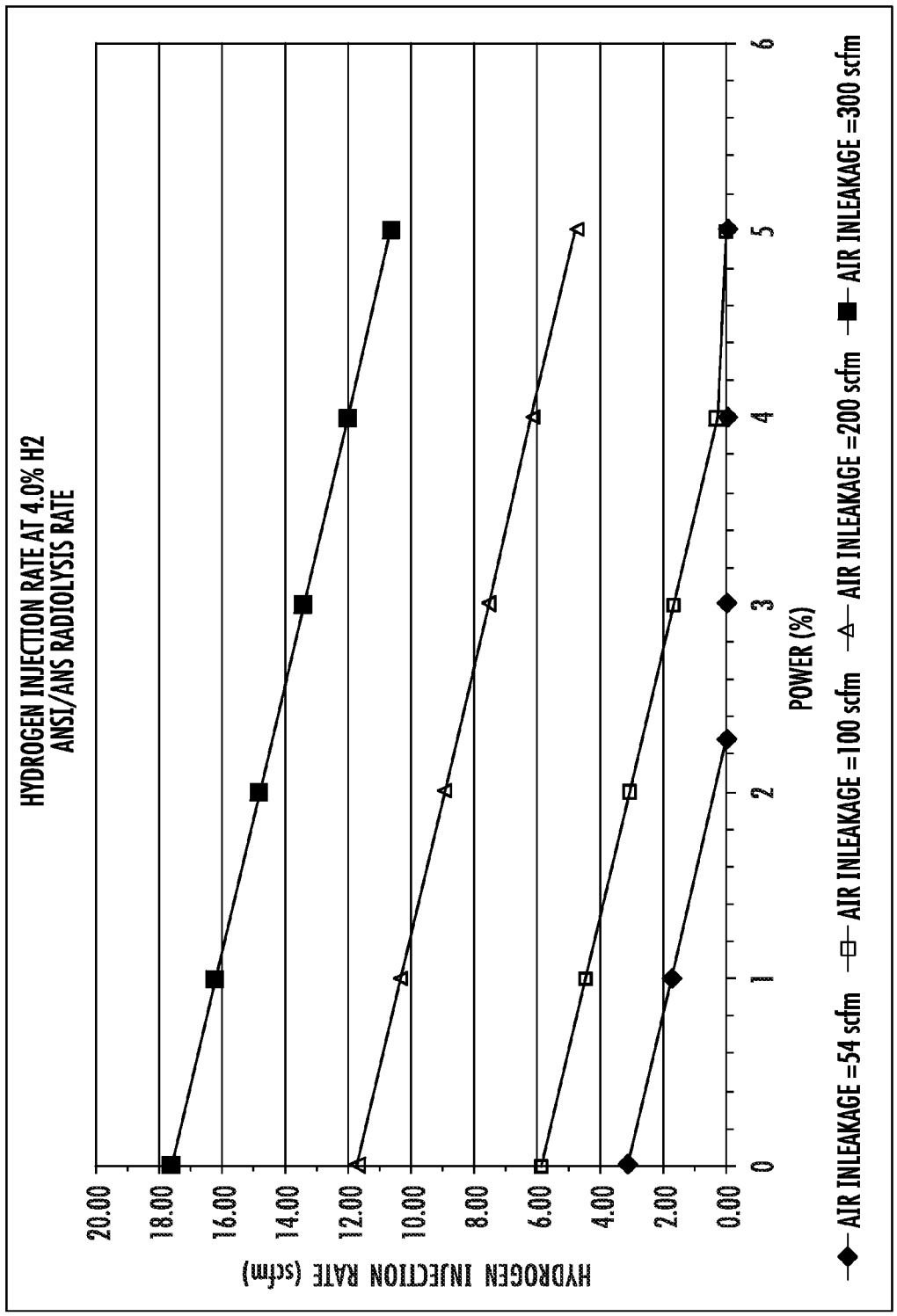
FIG. 18 shows estimated hydrogen injection rate for 4% $H_2$ condenser/off-gas hydrogen concentration.

The maximum hydrogen injection rate for EHWC with the MVP in service will depend on the off-gas flow and the limiting condenser/off-gas concentration. The off-gas flow is a combination of air in-leakage, water vapor and drawing air out of the condenser to reach normal vacuum. As the vacuum increases and more plant systems come on line, the in-leakage and off-gas flow will eventually reduce to normal values below 54 scfm (60 cfm). At the limiting concentration, the maximum hydrogen injection rate will decrease as power increases due to the hydrogen generated by radiolysis. The maximum hydrogen injection rates based on limiting condenser/off-gas concentrations to 8.0% (design case) and 4% (lower explosive limit in air) are shown in FIG. 17 and FIG. 18, respectively. Condenser Off-gas was assumed to be saturated with water vapor. The results indicate that based on a limit of 8.0% $H_2$, approximately 5 scfm hydrogen injection can be maintained from 0-5% power if the air in-leakage rate is 100 scfm or higher (FIG. 17). Based on a limit of 4.0% $H_2$, approximately 4 scfm hydrogen injection rate can be maintained from 0-5% power if the air in-leakage rate is 200 scfm or higher (FIG. 18).

Figure 19:
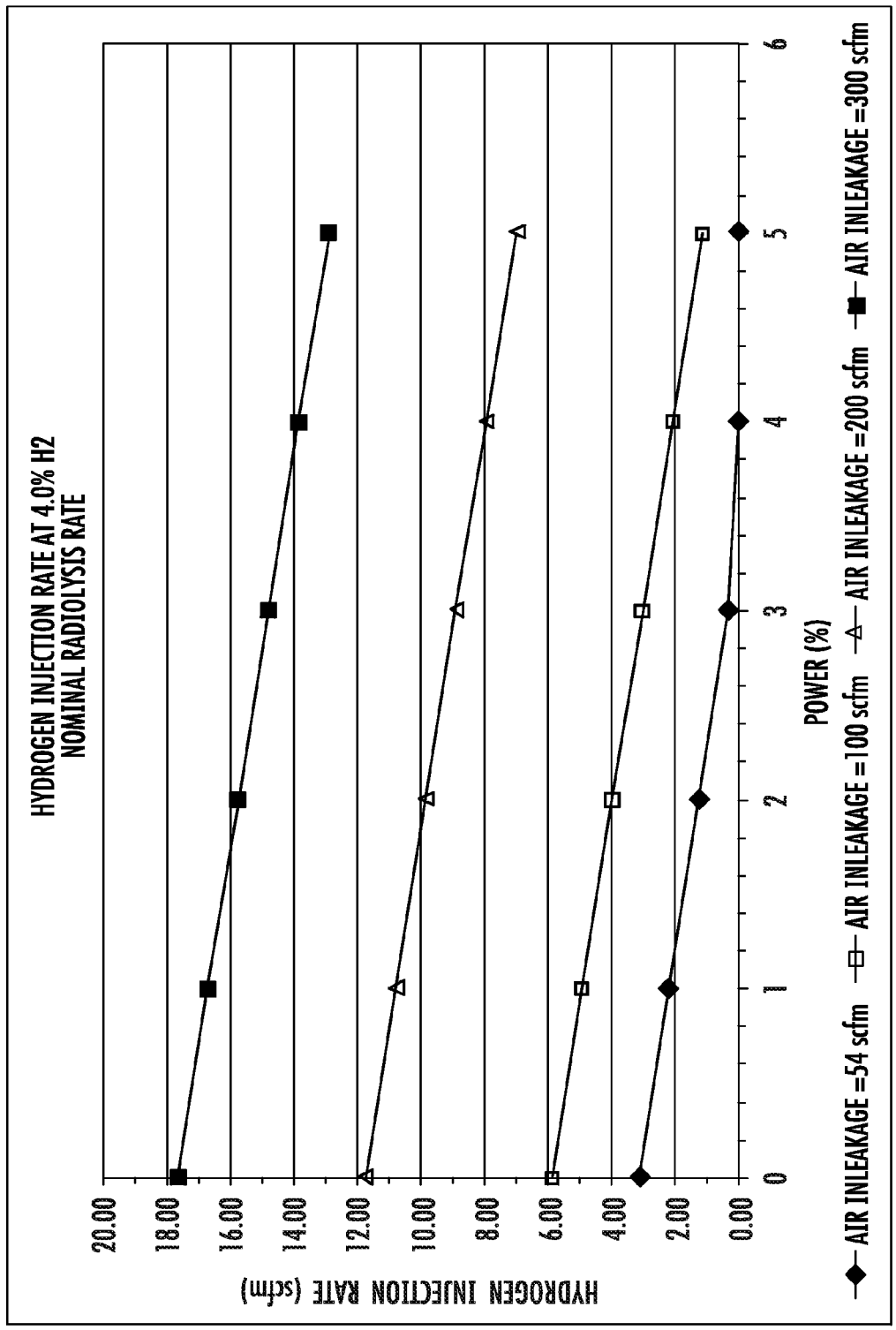
FIG. 19 shows estimated hydrogen injection rate for 4% $H_2$ condenser/off-gas hydrogen concentration.

The calculated hydrogen from radiolysis above was based on the ANSI/ANS design rate; however, the nominal radiolysis rate is ~⅔ of the ANSI/ANS design rate. The maximum hydrogen injection rates based on the nominal radiolysis rate and limiting condenser/off-gas concentrations to 4% (lower explosive limit in air) are shown in FIG. 19.

The normal off-gas system is placed in service at between 450 psig reactor pressure and 5% power. The normal HWC system is currently placed in service during startup at approximately 13% power. Oxygen injection into the off-gas preheater, upstream of the recombiner, starts when the normal HWC system is placed in service.

For continuation of EHWC from 5% power, after the transition from the MVP to the SJAEs, the required hydrogen injection rate is expected to be <2 scfm based on the normal hydrogen injection rate of 12.1 scfm at 100% power and assuming the required rate is proportional to power. At 2 scfm hydrogen injection, 1 scfm oxygen flow in excess of that generated by radiolysis would be required for recombination. An air in-leakage rate of 5 scfm or greater would satisfy this oxygen demand.

Baseline data were collected at startup for Cycle 18 following completion of RFO 17. The data provided useful benchmarks for plans and evaluations in support of the EHWC demonstration. The baseline data include off-gas flow, which is measured downstream of the recombiner, after the guard bed, and is indicative of the air in-leakage rate following the swap from the MVP to the SJAE.

Figure 20:
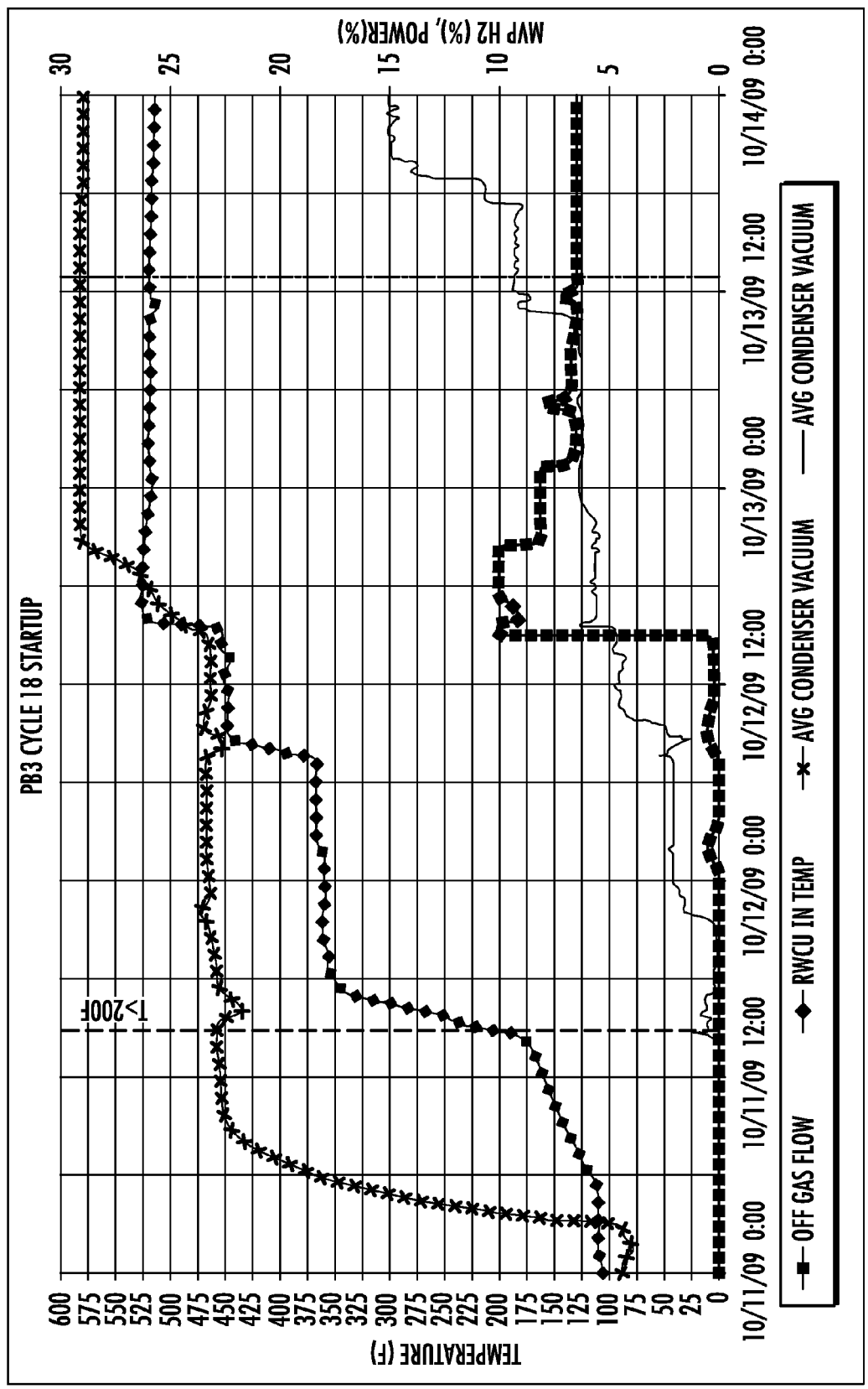
FIG. 20 shows a 3 cycle 18 startup off-gas flow.

Off-gas flow data downloaded from the plant process computer during the Cycle 18 startup are plotted in FIG. 20. Condenser vacuum, reactor water temperature and power trends are also plotted. The period of zero off-gas flow data shown up to ~5% power is when the MVP was in operation prior to placing normal off-gas in service. During this period of MVP operation, condenser vacuum ranged from 23-23.7"Hg.

The indicated off-gas flow rate increased to approximately 200 scfm on Oct. 12, 2009 at 15:00, as shown in FIG. 20 as the SJAEs were placed in service. The off-gas flow eventually settled out at 128 scfm. This is the expected response because the initial flow to the SJAEs will be high as the inventory of gas in the condenser is reduced in going from the MPV steady-state pressure of ~3.4 psia to the SJAE steady-state pressure of ~1 psia.

Example Off-Gas Recombiner System Calculations

Assumptions & Basic Data:
 1. 5% Min Reactor Load
 2. $H_2O$ Decomposition is Linear with Reactor Load
 3. Non-Condensible Off-Gas From SJAE@130° F. & 14.7 psia is:
   a. $H_2$—8 cfm
   b. $O_2$—4 cfm
   c. Air—60 cfm
 4. At 5% load reduced off-gas flow will cause jet compressor to pull vacuum on SJAE condenser of about 7 psig (7.7 psia)
 5. Vapor pressure of water at 130° F. is 2.2225 psia
Gas Constants for Non-Condensable Gases:
Individual Gas lb/mole mix
 1. $M_{H2}$=8/72*2=0.22 lb $H_2$/mole mix
 2. $M_{O2}$=4/72*32=1.78 lb $O_2$/mole mix
 3. $M_{Air}$=60/72*29=24.1 lb Air/mole mix
Total Mix lb/mole mix
 $M_{Mix}$=0.22+1.78+24.1=26.1 lb/mole mix
Individual Gas Constant=Universal Gas Constant/Molecular weight of the gas
 Universal Gas Constant=1545 ft lbf/lb-mole ° R
 1. $R_{H2}$=1545/2=766.8 [This value appears to be based on a MW of $H_2$ of 2.016]

2. $R_{O2}=1545/32=48.28$
3. $R_{Air}=1545/29=53.28$
4. $R_{vapor}=1545/18=85.83$
5. $R_{mix}=1545/26.1=59.2$ (This is for the above gas mixture)

Weight Rates of Non-Condensable Gases:

$$W = \frac{P*V}{R*T}$$

1. $W_{H2} = \frac{14.7*144*8}{766.8*590} = 0.037\frac{lb_{H2}}{min} = 2.25\frac{lb_{H2}}{hr}$ 2. $W_{O2} = \frac{14.7*144*4}{48.28*590} = 0.298\frac{lb_{O2}}{min} = 17.8\frac{lb_{O2}}{hr}$ 3. $W_{Air} = \frac{14.7*144*60}{53.28*590} = 4.04\frac{lb_{H2}}{min} = 242\frac{lb_{H2}}{hr}$ 4. Total = 2.25 + 17.8 + 242 = 262 lb/hr Weight of Water Vapor in Off-Gas:

$$W_{Vapor} = \frac{P_{Vapor}}{P_{Gas}} \times \frac{R_{Gas}}{R_{Vapor}} \times W_{Gas}$$

$$W_{Vapor} = \frac{2.2225}{7.7 - 2.2225} \times \frac{59.2}{85.8} \times 262 = 70.1\frac{lb}{hr} = 1.17\frac{lb}{min}$$

[Numbers in the calculation result in 73.35 lb/hr or 1.22 lb/min]

Volume of water vapor@130° F. & 14.7 psia $$V_{Vapor} = \frac{W_{Vapor} * R_{Vapor} * T}{P} = \frac{1.17 * 85.8 * 590}{14.7 * 144} = 27.9 \text{ cfm}$$

[Using 1.22 lb/min results in 29.2 cfm vapor]

Total flow@130° F. & 14.7 psia 8 cfm $H_2$+4 cfm $O_2$+60 cfm air+27.9 cfm vapor=99.9 cfm Percent Hydrogen 8 cfm $H_2$/99.9 cfm*100=8% $H_2$ The foregoing has described an apparatus and method to measure % $H_2$ in an MVP gas stream. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

We claim:

1. An apparatus adapted to measure gaseous hydrogen concentrations in a mechanical vacuum pump (MVP) gas stream, comprising first and second connection ports connected to an MVP system, where the MVP system includes a mechanical vacuum pump, to allow a gas stream sample to be taken from the MVP gas stream and a hydrogen concentration analyzer to measure $H_2$ concentrations of the gas stream sample taken from the MVP gas stream, wherein the first connection port is a gas stream sample intake connection port connected to a discharge side of the mechanical pump of the MVP system and the second connection port is a gas stream sample return connection port connected to a suction side of the mechanical pump of the MVP system.

2. The apparatus according to claim 1, further including a cart for supporting the apparatus and allowing the apparatus to be transported to a desired location.

3. The apparatus according to claim 1, further including a vacuum pump adapted to draw the gas stream sample from the MVP gas stream such that the gas stream sample flows through the hydrogen concentration analyzer for measurement of $H_2$ concentrations.

4. The apparatus according to claim 3, further including a relief valve adapted to open when a discharge pressure from the vacuum pump is greater than a pre-determined pressure.

5. The apparatus according to claim 1, further including a nitrogen purge regulator to allow a nitrogen supply to be used to purge the hydrogen concentration analyzer prior to conducting measurements of $H_2$ concentrations.

6. The apparatus according to claim 5, wherein the nitrogen purge regulator regulates a pressure of nitrogen being supplied to the hydrogen concentration analyzer.

7. The apparatus according to claim 1, further including a desiccant column adapted to remove moisture from the gas stream sample prior to entering the hydrogen concentration analyzer.

8. The apparatus according to claim 1, further including valves positioned at each of the connection ports to allow each port to be selectively opened or closed.

9. The apparatus according to claim 1, wherein the first connection port is a gas stream sample intake connection port and the second connection port is a gas stream sample return connection port.

10. A method for determining gaseous hydrogen concentrations in a mechanical vacuum pump (MVP) system gas stream, comprising the steps of:
   (a) providing an apparatus adapted to measure gaseous hydrogen concentrations in the mechanical vacuum pump (MVP) system gas stream having:
      (i) a hydrogen concentration analyzer; and
      (ii) first and second connection ports, the first connection port being a gas stream sample intake connection port and the second connection port being a gas stream sample return connection port;
   (b) connecting the apparatus to the MVP system using the first and second connection ports, wherein the first connection port is connected to a suction side or a discharge side of the MVP system and the second connection port is connected to a discharge side of the MVP system, wherein a flow pressure created by the mechanical vacuum pump forces the gas stream sample to enter the apparatus through the first connection port and exit the apparatus through the second connection port;
   (c) removing a gas stream sample from the MVP system gas stream, wherein a flow pressure created by a mechanical vacuum pump of the MVP system forces the gas stream sample to enter the apparatus through the first connection port and exit the apparatus through the second connection port; and
   (d) using the hydrogen concentration analyzer to determine $H_2$ concentrations in the gas stream sample.

11. The method according to claim 10, further including the step of using a nitrogen supply to purge the hydrogen concentration analyzer prior to removing the gas stream sample from the MVP system gas stream.

12. The method according to claim 10, wherein the apparatus further includes a vacuum pump to draw the gas stream sample from the MVP system gas stream.

13. The method according to claim 12, wherein the vacuum pump draws the gas stream sample through the first connection port and pumps the gas stream sample through the hydrogen concentration analyzer and back into the MVP system gas stream through the second connection port.

14. The method according to claim 10, wherein the first and second connection ports include valves.

15. The method according to claim 14, further including the step of selectively closing or opening the valves.

16. The method according to claim 10, further including the step of providing a desiccant column and using the desiccant column to remove moisture from the gas stream sample.

* * * * *